US006525067B1

(12) United States Patent
Chen

(10) Patent No.: US 6,525,067 B1
(45) Date of Patent: Feb. 25, 2003

(54) SUBSTITUTED HETEROCYCLIC DERIVATIVES

(75) Inventor: Yuhpyng Chen, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/708,858

(22) Filed: Nov. 8, 2000

Related U.S. Application Data

(60) Provisional application No. 60/167,162, filed on Nov. 23, 1999.

(51) Int. Cl.$^7$ .................. C07D 487/04; C07D 215/12; A61K 31/4709; A61K 31/47

(52) U.S. Cl. .................. 514/311; 514/314; 514/266.21; 514/256; 514/249; 514/255.05; 544/284; 544/333; 544/353; 544/405; 546/173; 546/176

(58) Field of Search ............... 546/173, 176; 514/311

(56) References Cited

U.S. PATENT DOCUMENTS

| | | | |
|---|---|---|---|
| 4,605,642 A | 8/1986 | Rivier et al. ............ | 514/12 |
| 5,063,245 A | 11/1991 | Abreu et al. ............ | 514/404 |
| 2001/0041673 A1 * | 11/2001 | Fossa .................... | 514/21 |

FOREIGN PATENT DOCUMENTS

| | | | |
|---|---|---|---|
| WO | WO 98/08846 | * | 3/1998 |
| WO | 9900373 | | 1/1999 |
| WO | 9938868 | | 8/1999 |

OTHER PUBLICATIONS

Simone, Oncology: Introduction, Cecil Textbook of Medicine, 20th Edition, vol. 1, pp. 1004–1010, 1996.*
Timothy W. Lovenberg, et al., Corticotropin–Releasing Factor Receptors: Inhibitors, Subtypes, Pharmacology, Localization, and Their Role in Central Nervous System Function, Current Pharmaceutical Designe, 1995, vol. 1, pp., 305–316, 1995.
Peter C. Wynn, et al., Regualtion of Corticotropin–Releasing Factor (CRF) Receptors in the Rat Pituitary Gland: Effects of Adrenalectomy on CRF Receptors and Corticotroph Responses, Endocrinology vol. 116, No. 4, pp. 1653–1659, 1985.
Dimitrie E. Grigoriadis, et al., Corticotropin–Releasing Factor (CRF) Receptors in Intermediate Lobe of the Pituitary: Biochemical Characterization and Autoradiographic Localization, Peptides, vol. 10 pp. 179–188, 1988.
William Pulsinelli, The Ischemic Penumbra in Stroke, Scientific American Science & Medicine, pp. 16–25, 1995.

Michael J. Owens, et al., Physiology and Pharmacology of Corticotropin–releasing Factor, vol. 43, No. 4, pp. 425–473, 1991.

* cited by examiner

Primary Examiner—Deepak Rao
(74) Attorney, Agent, or Firm—Peter C. Richardson; Paul H. Ginsburg; Kristina L. Konstas

(57) ABSTRACT

CRF antagonists of Formulas I–V, wherein the B group in the Formulas contains an oxime

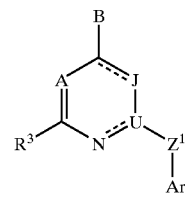

I

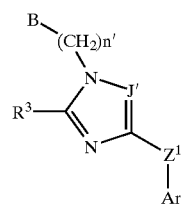

II

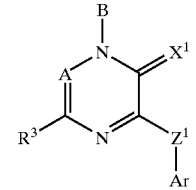

III

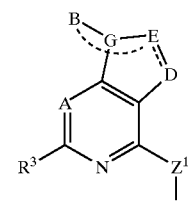

IV

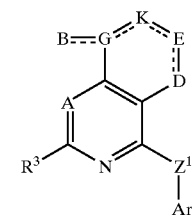

V

The variables in the Formulas have the meanings described herein.

11 Claims, No Drawings

SUBSTITUTED HETEROCYCLIC DERIVATIVES

This application claims priority under 35 U.S.C. §119(e) of U.S. application Ser. No. 60/167,162, filed Nov. 23, 1999, which application is hereby incorporated by reference herein.

BACKGROUND OF THE INVENTION

This invention relates to certain pharmaceutically active substituted heterocyclic derivatives, pharmaceutical compositions containing them and methods of administering them to subjects in need of their corticotropin releasing factor antagonist activity.

CRF antagonists are referred to in U.S. Pat. No. 4,605,642 (issued Aug. 12, 1986) and U.S. Pat. No. 5,063,245 (issued Nov. 5, 1991) and in International patent publications WO 95/33750 (published Dec. 14, 1995); WO 95/34563 (published Dec. 21, 1995); WO 94/13676 (published Jun. 23, 1994); WO 94/13677 (published Jun. 23, 1994); WO 95/33727 (published Dec. 14, 1995); WO 98/05661 (published Feb. 12, 1998); WO 98/08847 (published Mar. 5, 1998); and WO 98/08846 (published Mar. 5, 1998) and European patent publications EP 778277 (published Jun. 11, 1997) and EP 773023 (published May 14, 1997). CRF antagonists are also referred to in the following patent publications: EP 576350; WO 95/10506 (published Apr. 20, 1995); WO 96/35689 (published Nov. 14, 1996); WO 96/39400 (published Dec. 12, 1996); WO 97/00868 (published Jan. 9, 1997); WO 97/14684 (published Apr. 24, 1997); WO 97/29109 (published Aug. 14, 1997); WO 97/29110 (published Aug. 14, 1997); WO 97/35580 (published Oct. 2, 1997); WO 97/35846 (published Oct. 2, 1997); WO 97/44038 (published Nov. 27, 1997); WO 98/03510 (published Jan. 29, 1998); WO 98/08821 (published Mar. 5, 1998); WO 98/11075 (published Mar. 19, 1998); WO 98/15543 (published Apr. 16, 1998); WO 98/21200 (published May 22, 1998); WO 98/27066 (published Jun. 25, 1998); WO 98/29397 (published Jul. 9, 1998); WO 98/29413 (published Jul. 9, 1998); WO 98/42699 (published Oct. 1, 1998); WO 98/35967 (published Aug. 20, 1998); WO 98/45295 (published Oct. 15, 1998); WO 98/47874 (published Oct. 29, 1998); WO 98/47903 (published Oct. 29, 1998); WO 99/01454 (published Jan. 14, 1999); WO 99/01439 (published Jan. 14, 1999); WO 99/10350 (published Mar. 4, 1999); WO 99/12908 (published Mar. 18, 1999); WO 99/00373 (published Jan. 7, 1999); and WO 99/38868 (published Aug. 5, 1999).

The importance of CRF antagonists is set out in the literature, e.g., P. Black, Scientific American SCIENCE & MEDICINE, 1995, p. 16–25; T. Lovenberg, et al., Current Pharmaceutical Design, 1995, 1:305–316; and U.S. Pat. No. 5,063,245. An outline of activities possessed by CRF antagonists is found in M. J. Owens et al., Pharm. Rev., 1991, 43:425–473. CRF antagonists have been referred to as effective in the treatment of stress-related illnesses, mood disorders such as depression, major depressive disorder, single episode depression, recurrent depression, child abuse induced depression, postpartum depression, dysthemia, bipolar disorders; schizophrenia; cyclothymia; chronic fatigue syndrome; eating disorders such as anorexia and bulimia nervosa; generalized anxiety disorder; panic disorder; phobias; obsessive-compulsive disorder, post-traumatic stress disorder, pain perception such as fibromyalgia; headache; gastrointestinal diseases; hemorrhagic stress; ulcers; stress-induced psychotic episodes; fever; diarrhea; postoperative ileus; colonic hypersensitivity; irritable bowel syndrome; Crohn's disease; spastic colon; inflammatory disorders such as rheumatoid arthritis and osteoarthritis; pain; asthma; psoriasis; allergies; osteoporosis; premature birth; hypertension, congestive heart failure; sleep disorders; neurodegenerative diseases such as Alzheimer's disease, senile dementia of the Alzheimer's type, multiinfarct dementia, Parkinson's disease, and Huntington's disease; head trauma; ischemic neuronal damage; excitotoxic neuronal damage; epilepsy; stroke; spinal cord trauma; psychosocial dwarfism; euthyroid sick syndrome; syndrome of inappropriate antidiuretic hormone; obesity; chemical dependencies and addictions; drug and alcohol withdrawal symptoms; cancer; infertility; muscular spasms; urinary incontinence; hypoglycemia and immune dysfunctions including stress induced immune dysfunctions, immune suppression and human immunodeficiency virus infections; and stress-induced infections in humans and animals.

SUMMARY OF THE INVENTION

The present invention relates to a compound selected from Formulas I to V:

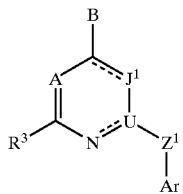

I

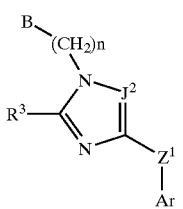

II

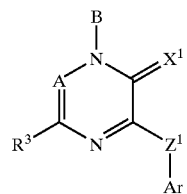

III

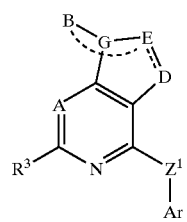

IV

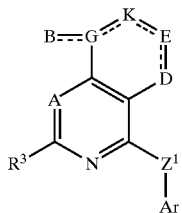

wherein:
the dashed lines in the figures represent optional double bonds;
n is 0 or 1;
A is nitrogen or $CR^7$;
B is $-C(R^2)(=NY^1R^1)$, $-(Y^3)-C(R^2)(=NY^1R^1)$, $-NR^{16}R^2$, $-NHCR^{16}R^2$, $-SCHR^{16}R^2$, $-CHR^{16}R^2$, $-C(OH)R^{16}R^2$, $-CHR^{16}(OR^{12})$, $-C(F)R^{16}R^2$, $-C(OMe)R^{16}R^2$, $-CR^{16}(=CR^2R^1)$, $-CHR^{16}(NR^1)$, $=C(R^2)(R^{16})$, $-C(N(C_0-C_4alky)R^2)(=NY^1R^1)$, $-Y^3C(Y^2R^2)(=NY^1R^1)$, $-C(R^2)(NR^{14}C(=X^2)NR^1R^{15})$, $-C(R^2)(OC(=X^2)NR^1R^{15})$, $-C(R^2)(NR^{14}C(=X^2)R^{15})$, or $-V^1-V^2$, provided that B may be $=C(R^2)(R^{16})$ only in the compounds of Formulas IV and V and only where G is carbon in the compounds of Formulas IV and V;
$J^1$ and $J^2$ are independently nitrogen or $CR^5$; or $J^1$ or $J^2$ optionally connects to $Z^1$ to form a compound of Formula VI to IX;

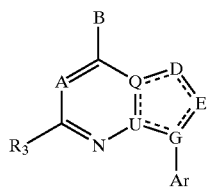

VI

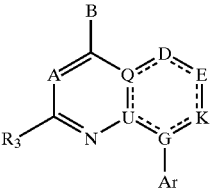

VII

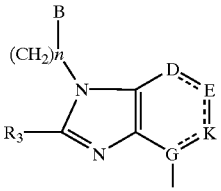

VIII

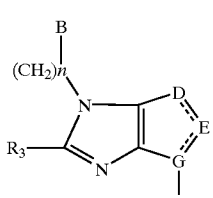

IX

Q and U are independently nitrogen or carbon provided that Q and U are not both nitrogen;

$V^1$ is ($C_0$–$C_1$ alkylene), O, S, NH, or $-N(C_1$–$C_4$ alkylene);
$V^2$ is a five to eight membered carbocyclic ring wherein one or two of the carbocyclic ring carbons may optionally and independently be replaced by O, S, N, or $NZ^3$, and the ring optionally contains one to three double bonds, further wherein the ring is optionally substituted with from one to two $R^{22}$ substituents and wherein the ring or $R^{22}$ comprises the moiety $C=N-Y^1-(C_1-C_4$ alkylene);
$X^1$ is O, S, $=NOH$, $=NO(C_1-C_4$ alkyl), or $=C(H)(R^5)$, $=C(C_1-C_4$ alkyl)$(R^5)$, wherein said $C_1-C_4$ alkyl in said $X^1$ group is optionally substituted with F, $-O(C_1-C_4$ alkyl), $-OCF_3$, $-OCHF_2$, or OH; or $X^1$ may bond to $Z^1$ to form a compound of Formula X or XI:

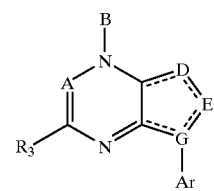

X

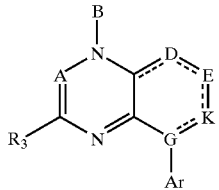

XI $X^2$ is S or O;
$Y^1$, $Y^2$, and $Y^3$ are each independently O, S, NH, or $-N(C_1-C_4$ alkyl);
$Z^1$ is O, S, NH, $-N(C_1-C_2$ alkyl), $NCOCF_3$, NCO $(C_1-C_2$ alkyl), or $-C(R^{11})(R^{12})$, or $Z^1$ may bond to $J^1$, $J^2$, or $X^1$ to form said compounds of Formulas VI to XI, or $Z^1$ may bond to Ar at the ortho position of Ar to form a five or six membered fused ring in the compounds of Formulas XII to XV:

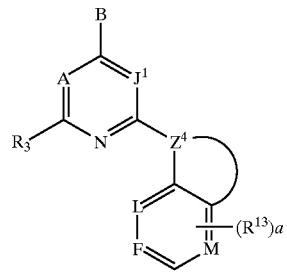

XII

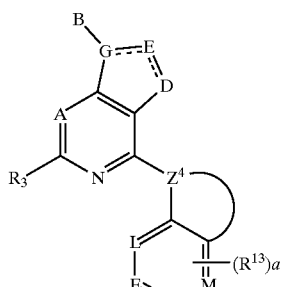

XIII

-continued

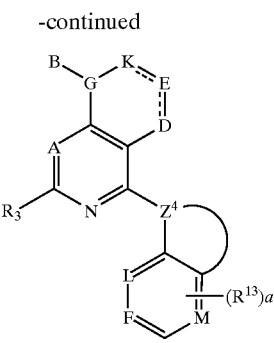

XIV

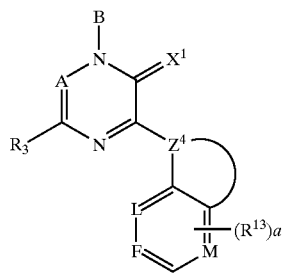

XV wherein:

D and E are independently selected from nitrogen and $CR^4$ when double bonded to any adjacent ring atom, or are independently selected from C=O, C=S, sulfur, oxygen, $C(R^4)(R^6)$, and $NR^8$ when single bonded to both adjacent ring atoms;

F, M, and L are independently nitrogen or carbon, wherein the ring containing F, M, and L is selected from phenyl, pyridyl, pyrimidyl, pyrazinyl, and pyridazinyl;

K is selected from nitrogen and $CR^6$ when it is double bonded to any adjacent ring atom, or K is selected from oxygen, sulfur, C=O, C=S, $CR^6R^{12}$, and $NR^8$ when it is single bonded to both adjacent atoms, or K is two bonded atoms, wherein one of the atoms is oxygen, sulfur, nitrogen, $CR^6$, C=O, C=S, $CR^6R^{12}$, or $NR^8$, and the other is $CR^9$ or $CR^6R^{12}$;

G is nitrogen or carbon, provided that when G is nitrogen it is single bonded to the adjacent E or K and when G is carbon it is double bonded to the adjacent E or K, further provided that G may be a double bonded to B only where G is carbon, and that where G is double bonded to B, it is single bonded to E in Formulas IV and XIII and single bonded to K in Formulas V and XIV and further where G is double bonded to B, B is $C(R^2)(R^{16})$;

wherein the ring containing D, E, K, G, in Formula VII, VIII, or XI optionally has from one to three double bonds, from zero to two heteroatoms, and from zero to two C=O or C=S groups;

and wherein the ring containing D, E, G atoms in Formula VI, IX, or X optionally has one to two double bonds;

further wherein when $Z^1$ connects to the ortho position of Ar to form a five or six membered ring of a compound of Formulas XII to XV, the ring optionally contains from one to two double bonds, and wherein one or two of the carbon atoms of said five- to six-membered ring of Formulas XII to XV may optionally and independently be replaced by an oxygen or sulfur atom or by $NZ^2$;

$Z^2$ is hydrogen or $C_1$–$C_4$ alkyl;

$Z^3$ is hydrogen, $C_1$–$C_4$ alkyl, or benzyl;

$Z^4$ is N, CH, or $C(C_1$–$C_2$ alkyl) when single bonded to both adjacent ring atoms, and $Z^4$ is carbon when double bonded to either adjacent ring atom;

a is from one to four;

Ar is $C_6$–$C_{10}$ aryl or 5–10 membered heteroaryl, wherein Ar is optionally substituted with from one to four $R^{13}$ substituents, and wherein two adjacent $R^{13}$ substituents optionally form a five to seven membered ring structure fused to Ar, which five to seven membered ring may be further substituted with from one to four independently selected $R^{13}$ substituents, and which five to seven membered ring opbonally contains one to three double bonds and one to three heteroatoms selected from O, S, N, and $NZ^3$, further wherein Ar may bond to $Z^1$ at the ortho position of Ar to form said compounds of Formulas XII to XV;

$R^1$ is H, $C_1$–$C_6$ alkyl, $C_6$–$C_{10}$ aryl, 5–10 membered heteroaryl, ($C_1$–$C_6$ alkylene)-($C_6$–$C_{10}$ aryl), ($C_1$–$C_6$ alkylene)-(5–10 membered heteroaryl), $C_3$–$C_8$ cycloalkyl, ($C_1$–$C_6$ alkylene)-($C_3$–$C_8$ cycloalkyl), $C_3$–$C_8$ spiroalkyl, $C_3$–$C_8$ heterocycloalkyl, or ($C_1$–$C_4$ alkylene)-($C_3$–$C_8$ heterocycloalkyl), wherein each of said $R^1$ groups is optionally substituted with one or two substituents independently selected from hydroxy, fluoro, chloro, bromo, iodo, $C_1$–$C_6$ alkyl, alkoxy, $CF_3$, —C(=O)O—($C_1$–$C_4$ alkyl), —OC(=O)($C_1$–$C_4$ alkyl), $C_1$–$C_6$ alkyl, $C_3$–$C_8$ cycloalkyl, —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —$CONH_2$, —CONH($C_1$–$C_4$ alkyl), —CON($C_1$–$C_4$ alkyl)($C_1$–$C_2$ alkyl), —S($C_1$–$C_4$ alkyl), CN, —$NO_2$, —SO($C_1$–$C_4$ alkyl), —$SO_2$($C_1$–$C_4$ alkyl), —$SO_2$NH($C_1$–$C_4$ alkyl) —$SO_2$N($C_1$–$C_4$ alkyl)($C_1$–$C_2$ alkyl), and $NR^{17}R^{18}$, wherein each of the alkyl moieties of said $R^1$ groups that contains three or more carbons optionally contains one or two double or triple bonds and wherein each of the $C_1$–$C_2$ alkyl moieties in said $R^1$ groups optionally contains one double or triple bond, provided that when $Y^1$ is S, or O, and $Y^1$ is attached to $R^1$, then $R^1$ is not H;

$R^2$ is H, $C_1$–$C_6$ alkyl, $C_6$–$C_{10}$ aryl, 5–10 membered heteroaryl, ($C_1$–$C_6$ alkylene)-$Y^1$—($C_1$–$C_6$ alkyl), ($C_1$–$C_6$ alkylene)-($C_6$–$C_{10}$ aryl), ($C_1$–$C_6$ alkylene)-(5–10 membered heteroaryl), $C_3$–$C_8$ cycloalkyl, ($C_1$–$C_6$ alkylene)-($C_3$–$C_8$ cycloalkyl), wherein each of said $R^2$ groups is optionally substituted with from one to three substituents independently selected from chloro, fluoro and $C_1$–$C_4$ alkyl, or with one substituent selected from hydroxy, bromo, iodo, $C_1$–$C_6$ alkoxy, —OC(=O)($C_1$–$C_6$ alkyl), —OC(=O)NH($C_1$–$C_4$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl) and —$SO_2$N($C_1$–$C_4$ alkyl)($C_1$–$C_2$ alkyl), provided that when $Y^2$ is S, or O, then $R^2$ is not H;

$R^3$ is hydrogen, $C_1$–$C_4$ alkyl, —O($C_1$–$C_4$ alkyl), chloro, fluoro, bromo, iodo, $CF_3$, ($C_1$–$C_2$ alkylene) O($C_1$–$C_2$ alkyl), ($C_1$–$C_2$ alkylene)-OH, —S($C_1$–$C_4$ alkyl) or —$SO_2$($C_1$–$C_4$ alkyl);

$R^4$ and $R^6$ are each independently hydrogen, OH, ($C_1$–$C_6$ alkyl), or one of $R^4$ or $R^6$ is hydrogen, ($C_1$–$C_4$ alkyl), $CF_3$, $CH_2CF_3$, $CF_2CF_3$, and the other is —CO($C_1$–$C_4$ alkyl), —S($C_1$–$C_2$ alkyl), —O($C_1$–$C_4$ alkyl), or —NH($C_1$–$C_4$ alkyl), wherein adjacent substituents at D and E may optionally form a 5 to 6 membered carbocyclic or heterocyclic ring fused to the bicyclic ring containing D and E, wherein said heterocyclic ring contains 1 to 3 heteroatoms, and wherein $CR^4R^6$ optionally forms a $C_3$–$C_5$ carbocyclic ring wherein one member of said $C_3$–$C_5$ carbocyclic ring may optionally be replaced with O;

$R^5$ is hydrogen, $C_1$–$C_6$ alkyl, fluoro, chloro, bromo, iodo, hydroxy, cyano, amino, ($C_1$–$C_2$ alkylene)-OH, ($C_1$–$C_2$ alkylene)-O($C_1$–$C_4$ alkyl), —$CH_2OCF_3$, $CF_3$, —$CH_2SMe$, —S($C_1$–$C_3$ alkyl), nitro, —O($C_1$–$C_4$ alkyl), —N($C_1$–$C_4$ alkyl)($C_1$–$C_2$ alkyl), —S($C_1$–$C_4$ alkyl), —C(=O)($C_1$–$C_4$ alkyl), —C(=NOH)($C_1$–$C_4$ alkyl), —C(=NO—($C_1$–$C_4$ alkyl))($C_1$–$C_4$ alkyl), —C(=O)H, —C(=O)O ($C_1$–$C_4$alkyl), —$CONR^{17}R^{18}$, wherein each of the $C_1$–$C_4$ alkyl moieties of $R^5$ optionally contains one double or triple bond and is optionally substituted with one substituent selected from hydroxy, amino, $NHCOCH_3$, NH($C_1$–$C_2$ alkyl), and N($C_1$–$C_2$ alkyl)$_2$;

$R^7$ is hydrogen, $C_1$–$C_4$ alkyl, chloro, fluoro, iodo, bromo, hydroxy, —O($C_1$–$C_4$ alkyl), —C(=O)($C_1$–$C_4$ alkyl), —C(=O)O($C_1$–$C_4$ alkyl), —$OCF_3$, —$CF_3$, —$CH_2OH$ or —$CH_2O$($C_1$–$C_2$ alkyl);

$R^8$, $R^9$, and $R^{10}$ are independently hydrogen or $C_1$–$C_4$ alkyl;

$R^{11}$ and $R^{12}$ are independently hydrogen, trifluoromethyl or methyl, or one of $R^{11}$ and $R^{12}$ is cyano and the other is hydrogen or methyl;

$R^{13}$ is fluoro, chloro, iodo, bromo, $C_1$–$C_6$ alkyl, $C_3$–$C_8$ cycloalkyl, ($C_1$–$C_4$ alkylene)-($C_3$–$C_8$ cycloalkyl), —O($C_1$–$C_6$ alkyl), —O($C_3$–$C_8$ cycloalkyl), —O—($C_1$–$C_4$ alkylene)-($C_3$–$C_8$ cycloalkyl), formyl, OH, $OCF_3$, $OCHF_2$, ($C_1$–$C_4$ alkylene)-OH, ($C_1$–$C_4$ alkylene)-O—($C_1$–$C_2$ alkyl), —CN, —$CF_3$, $CHF_2$, $NO_2$, —$NH_2$, —NH($C_1$–$C_4$ alkyl), —N($C_1$–$C_2$ alkyl)($C_1$–$C_6$ alkyl), —OC(=O)($C_1$–$C_4$ alkyl), ($C_1$–$C_4$ alkylene)-O—($C_1$–$C_4$ alkyl), —S($C_1$–$C_6$ alkyl), ($C_1$–$C_4$ alkylene)-S—($C_1$–$C_4$ alkyl), —C(=O)O($C_1C_4$ alkyl), —C(=O)($C_1$–$C_4$ alkyl), ($C_0$–$C_2$ alkylene)-C(=N—O($C_0$–$C_4$ alkyl)), —COOH, —$SO_2NH$($C_1$–$C_4$ alkyl), —$SO_2N$($C_1$–$C_2$ alkyl)($C_1$–$C_4$ alkyl), —$SO_2NH_2$, —$NHSO_2$($C_1$–$C_4$ alkyl), —S($C_1$–$C_6$ alkyl), —$SO_2$($C_1$–$C_6$ alkyl), —$CONR^{17}R^{18}$, ($C_1$–$C_2$ alkylene)$NR^{17}R^1$ and $C_3$–$C_8$ carbocyclic ring in which one or two carbon atoms may be replaced with O, S, or N to form a heterocyclic ring and wherein said carbocyclic or heterocyclic ring may optionally contain one to three double bonds, and wherein each of the $C_1$–$C_4$ alkyl and $C_1$–$C_6$ alkyl moieties in said $R^{13}$ group optionally has one or two double bonds, and said $C_1$–$C_4$ alkylene and said $C_1$–$C_6$ alkyl in said $R^{13}$ group is optionally substituted with $C_1$–$C_4$ alkyl or F;

$R^{14}$ and $R^{15}$ are independently selected from H, $C_1$–$C_4$ alkyl, —$CH_2$($C_3$–$C_8$ cycloalkyl), and $C_3$–$C_8$ cycloalkyl;

$R^{16}$ is —$R^{19}$—C(=N—$Y^1R^1$)—$R^{20}$, wherein each alkyl or alkylene group in said $R^{16}$ group optionally contains one or two double or triple bonds;

$R^{17}$ and $R^{18}$ are independently H, $C_1$–$C_6$ alkyl, or $C_3$–$C_8$ heterocycloalkyl; or $NR^{17}R^{18}$ forms a $C_4$–$C_6$ heterocyclo ring which is optonally substituted with hydrogen, $C_1$–$C_6$ alkyl, $CONH_2$, CO[N($C_0$–$C_4$ alkyl)($C_0$–$C_4$ alkyl)], or $C_4$–$C_8$ heterocycloalkyl;

$R^{19}$ is $C_1$–$C_6$ alkylene, ($C_1$–$C_6$ alkylene)-$Y^1$-(alkylene), CO, CS, SO, $SO_2$, wherein said alkylene is optionally substituted with hydroxy, fluoro, chloro, bromo, iodo, $C_1$–$C_4$ alkoxy, $CF_3$, $CHF_2$, O—$CF_3$, $OCHF_2$, —C(=O)O—($C_1$–$C_4$ alkyl), —OC(=O) ($C_1$–$C_4$ alkyl), —OC(=O)N($C_1$–$C_4$ alkyl)($C_1$–$C_2$ alkyl), —NHCO($C_1$–$C_4$ alkyl), —COOH, —COO ($C_1$–$C_4$ alkyl), —CONH($C_1$–$C_4$ alkyl), —CON ($C_1$–$C_4$ alkyl)($C_1$–$C_2$ alkyl), —S($C_1$–$C_4$ alkyl), CN, —$NO_2$, —SO($C_1$–$C_4$ alkyl), —$SO_2$($C_1$–$C_4$ alkyl), —$SO_2NH$($C_1$–$C_4$ alkyl) or —$SO_2N$($C_1$–$C_4$ alkyl) ($C_1$–$C_2$ alkyl);

$R^{20}$ is hydrogen, $C_1$–$C_4$ alkyl, ($C_0$–$C_4$ alkylene)-$NR^{17}R^{18}$, or ($C_1$–$C_6$ alkylene)-G—$R^{21}$, wherein G is oxygen or sulfur;

$R^{21}$ is hydrogen, $CF_3$, or $C_1$–$C_4$ alkyl; and $R^{22}$ is hydrogen, $C_1$–$C_4$ alkyl, —O($C_1$–$C_4$ alkyl), chloro, fluoro, bromo, iodo, $CF_3$, ($C_1$–$C_2$ alkylene) O($C_1$–$C_2$ alkyl), ($C_1$–$C_2$ alkylene)-OH, —S($C_1$–$C_4$ alkyl), —$SO_2$($C_1$–$C_4$ alkyl); or C=N—$Y^1$—($C_1$–$C_4$ alkyl);

provided that in the five, six or seven membered rings of any of the above Formulae, there are not two adjacent double bonds and not two adjacent oxygen atoms;

and wherein, unless otherwise indicated, heteroaryl contains one to five heteroatoms selected from S, SO, $SO_2$, O, N, and $NZ^3$ and contains no S—S, O—O, or S—O bonds, and heterocyclyl contains one to four heteroatoms selected from O, S, N, or $NZ^3$, and one to three double bonds, and alkyl, alkoxy, spiroalkyl, cycloalkyl, and heterocycloalkyl optionally contain from one to three double or triple bonds;

and the pharmaceutically acceptable salts and prodrugs of the compound.

It is understood according to conventional organic chemistry rules that in the above formulae I to XV wherein nitrogen is attached to adjacent atoms by a total of three bonds (i.e., a trivalent bond); similarly, carbon has four bonds (i.e., a tetravalent bond), and oxygen has two bonds (i.e., a bivalent bond). It is also understood that an alkyl moiety must have at least two carbon atoms to contain a double or triple bond and must have at least four carbon atoms to contain two double or triple bonds, and that no carbon atom in the chain can be double bonded to more than one other carbon atom in the chain.

In one embodiment of the invention, the compound is of the Formula VI wherein A is N and Q, U, D, G, and E form a pyrrolo or pyrazolo ring.

In another embodiment, the compound is of the Formula VI wherein A is CH, CMe, and Q, U, D, G, and E form a pyrrolo or pyrazolo ring.

In another embodiment, the compound is of the Formula I wherein the ring containing A, J, and U is a pyridine ring, and $Z^1$ is O or S.

In another embodiment, the compound is of the Formula I wherein the ring containing A, J, and U is a pyridine ring, and $Z^1$ is NH or $CH_2$.

In another embodiment, the compound is of the Formula I wherein the ring containing A, J, and U is a pyrimidine ring, and $Z^1$ is O, S, or NH.

In a further embodiment, the compound is of the Formula VII wherein A is N and the ring containing Q, U, D, E, K, and G is a dihydro-oxazino ring.

In a further embodiment, the compound is of the Formula VII wherein A is CH and the ring containing Q, U, D, E, K, and G is a dihydro-oxazino ring.

The invention also relates to the embodiment wherein the compound is of the Formula VII and Q and U are carbon. It further relates to the embodiment wherein the compound is of the Formula VII, and A is $CR^7$, and D and E are $CR^4$ or $C(R^4)(R^6)$.

In one embodiment, the compound is of the Formula VII wherein A is N.

In one embodiment of the compounds, B is $—C(R^2)(=N—O—R^1)$.

In another embodiment, B is $—C(R^2)(=N—NH—R^1)$, or $—C(R^2)(=N—N(C_1-C_4\ alkyl)R^1)$.

In further embodiments of the invention, B is $—C(R^2)(OC(=O)NR^1R^{15})$, $—C(R^2)(NR^{14}C(=O)NR^1R^{15})$ or $NR^{16}R^2$.

In another embodiment, $V^2$ is selected from structures XVI–XX:

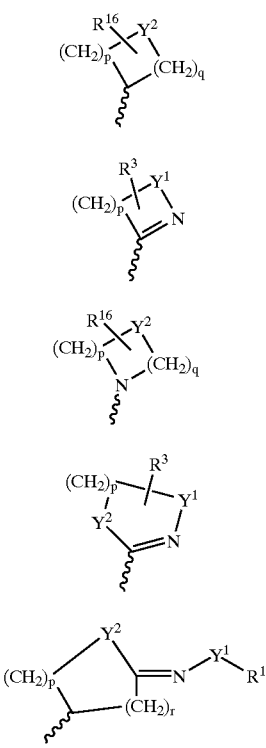

XVI

XVII

XVIII

XIX

XX wherein p is 0–3, r is 0–2, and q is 1–3.

In another embodiment, the compound is of Formula VII, VIII, or XI wherein the ring containing D, E, K, G is a 6-membered aromatic/heteroaromatc ring selected from benzo, pyrido, pyridazino, or pyrimido.

In one example of this embodiment, the compound is of Formula VII and the ring containing D, E, K, G is a benzo ring, particularly also where A is a CH or CMe, or A is N. In a further preferred embodiment, and particularly of this embodiment, $R^2$ is aryl, $C_1-C_4$ alkyl, $C_3-C_8$ cycloalkyl, $C_3-C_8$ heterocycloalkyl, $(C_1-C_4\ alkyl)-C_3-C_8$ heterocycloalkyl), $(C_1-C_4\ alkylene)-O-(C_1-C_4\ alkyl)$, $CF_3$, or $CF_2CF_3$. In one embodiment, $R^2$ is thiazolyl, pyridyl, $C_1-C_4$ alkyl, or $CF_3$. In another aspect of the invention, and particularly of this embodiment, $R^1$ is preferably $C_1-C_4$ alkyl, $C_3-C_8$ cycloalkyl, $(C_1-C_4\ alkylene)-O-(C_1-C_4\ alkyl)$, $—C_1-C_4$ alkyl-OH.

In another embodiment, Ar is phenyl, thiazolyl, naphthyl, thienyl, benzothienyl, pyridyl, quinolyl, quinazolinyl, quinoxalinyl, pyrazinyl, pyrimidinyl, imidazolyl, furanyl, benzimidazolyl, benzofuranyl, benzothiazolyl, benzisoxazolyl, isothiazolyl, pyrazolyl, pyrrolyl, indolyl, pyrrolopyridyl, oxazolyl and benzoxazolyl, or benzothiadiazole. Preferably, Ar is phenyl or pyridyl.

In another embodiment, Ar, particularly wherein Ar is phenyl, has two or three $R^{13}$ substituents independently selected from $C_1-C_4$ alkyl, $C_3-C_8$ cycloalkyl, $(C_1-C_2$ alkylene)-$(C_3-C_8$ cycloalkyl), $—O—(C_1-C_2$ alkylene)$(C_3-C_8$ cycloalkyl), $—O—(C_3-C_8$ cycloalkyl), $—O—(C_1-C_4$ alkyl), $(C_1-C_4\ alkylene)-O—(C_1-C_4\ alkyl)$, $CF_3$, $—OCF_3$, $—CHO$, $(C_1-C_4\ alkylene)-OH$, $—C(OH)(C_1-C_4\ alkyl)(C_1-C_4\ alkyl)$, cyano, chloro, fluoro, bromo and iodo, wherein each of the foregoing $(C_1-C_4)$ alkyl groups optionally contains one double or triple bond.

In another embodiment wherein two adjacent $R^{13}$ substituents optionally form a five to seven membered ring structure fused to Ar, the ring structure that is fused is a dioxoalkylene ring or dioxane ring, or a morpholino, piperidino, piperazino, pyrrolidino, oxodiazo, or thiadiazo ring.

In yet another embodiment, $R^3$ is $C_1-C_4$ alkyl, chloro, fluoro, bromo, iodo or $—O—(C_1-C_4)$ alkyl.

In another embodiment, $R^1$ is H, $C_1-C_4$ alkyl, $C_3-C_8$ cycloalkyl, $(C_1-C_4\ alkylene)-O—(C_1-C_4\ alkyl)$, or $—C_1-C_4$ alkyl-OH.

In a further embodiment, $R^1$ is H, $C_1-C_4$ alkyl, $(C_1-C_4\ alkylene)-OH$, or $(C_1-C_4\ alkylene)-O—(C_1-C_4\ alkyl)$, $R^2$ is methyl, ethyl, pyridin-2-yl, or trifluoromethyl, $R^3$ is methyl, each of $R^4$ and $R^6$ is, independently, hydrogen or methyl, and $R^{13}$ is methyl.

In another embodiment, $R^1$ is H or $C_1-C_4$ alkyl, $R^2$ is methyl, ethyl, pyridin-2-yl, or trifluoromethyl, $R^3$ is methyl, $R^4$ is hydrogen or methyl, $R^7$ is H or methyl, $R^{13}$ is methyl, $R^{14}$ and $R^{15}$ are independently H or $C_1-C_4$ alkyl, and $R^{16}$ does not contain any optional double or triple bond.

In another embodiment, $R^2$ is $C_1-C_4$ alkyl and $R^{16}$ is $(C_1-C_2\ alkylene)-C[=NO(C_0-C_2\ alkyl)](C_1-C_2\ alkyl)$.

In another embodiment, B is $—C(R^2)(=NOR^1)$, wherein $R^2$ is $C_1-C_4$ alkyl, pyridyl, thiazolyl, $CF_3$, $CF_3CF_2$, and $R_1$ is H or $C_1-C_4$alkyl.

In another embodiment, B forms a five membered heterocyclic ring.

In a further embodiment, B is thiazolidino ring with a substituent of $(C_0-C_2\ alkylene)-C[=NO(C_0-C_2\ alkyl)](C_1-C_2\ alkyl)$.

In another embodiment, B comprises a tetrahydrofurano ring with a substituent of $(C_0-C_2\ alkylene)-[=NO(C_0-C_2\ alkyl)](C_1-C_2\ alkyl)$.

Following are examples of compounds of the invention:

(E)-1-[2,5,6-Trimethyl-7-(2,4,6-trimethyl-phenyl)-7H-pyrrolo[2,3-d]pyrimidin-4-yl]-propan-1-one oxime;

(Z)-1-[2,5,6-Trimethyl-7-(2,4,6-trimethyl-phenyl)-7H-pyrrolo[2,3-d]pyrimidin-4-yl]-propan-1-one oxime;

5-Hydroxy-4-(1-hydroxyimino-propyl)-2,5-dimethyl-7-(2,4,6-trimethyl-phenyl)-5,7-dihydro-pyrrolo[2,3-d]pyrimidin-6-one;

1-[2-Methyl-8-(2,4,6-trimethyl-phenyl)-quinolin-4-yl]-propan-1-one (E)-oxime;

1-[2-Methyl-8-(2,4,6-trimethyl-phenyl)-quinolin-4-yl]-propan-1-one (Z)-oxime;

1-[2-Methyl-8-(2,4,6-trimethyl-phenyl)-quinolin-4-yl]-propan-1-one (E)-O-methyl-oxime;

1-[2-Methyl-8-(2,4,6-trimethyl-phenyl)-quinolin-4-yl]-propan-1-one O-methyl-oxime;

(E)-1-[3,6-Dimethyl-2-(2,4,6-trimethyl-phenoxy)-pyridin-4-yl]-propan-1-one O-methyl-oxime;
(Z)-1-[3,6-Dimethyl-2-(2,4,6-trimethyl-phenoxy)-pyridin-4-yl]-propan-1-one O-methyl-oxime;
1-[7-Methyl-1-(2,4,6-trimethyl-phenyl)-1,4-dihydro-2H-pyrimido[4,5-d][1,3]oxazin-5-yl]-propan-1-one (E)-oxime;
1-[7-Methyl-1-(2,4,6-trimethyl-phenyl)-1,4-dihydro-2H-pyrimido[4,5-d][1,3]oxazin-5-yl]-propan-1-one (Z)-oxime;
1-[2,5,6-Trimethyl-7-(2,4,6-trimethyl-phenyl)-7H-pyrrolo[2,3-d]pyrimidin-4-yl]-ethanone (E)-O-methyl-oxime;
1-[2,5,6-Trimethyl-7-(2,4,6-trimethyl-phenyl)-7H-pyrrolo[2,3-d]pyrimidin-4-yl]-ethanone (Z)-O-methyl-oxime;
[2-(4-Chloro-2,6-dimethyl-phenoxy)-3,6-dimethyl-pyridin-4-yl]-pyridin-2-yl-methanone (Z)-oxime;
1-[2-Methyl-(2,4,6-trimethyl-phenyl)-quinolin-4-yl]-propan-1-one O-isobutyl-oxime;
(Z)-1-[2,5,6-Trimethyl-7-(2,4,6-trimethyl-phenyl)-7H-pyrrolo[2,3-d]pyrimidin-4-yl]-propan-1-one oxime;
5-Hydroxy-4-(1-hydroxyimino-propyl)-2,5-dimethyl-7-(2,4,6-trimethyl-phenyl)-5,7-dihydro-pyrrolo[2,3-d]pyrimidin-6one;
1-[2-Methyl-8-(2,4,6-trimethyl-phenyl)-quinolin-4-yl]-propan-1-one (E)-oxime;
1-[2-Methyl-8-(2,4,6-trimethyl-phenyl)-quinolin-4-yl]-propan-1-one (Z)-oxime;
1-[2-Methyl-8-(2,4,6-trimethyl-phenyl)-quinolin-4-yl]-propan-1-one (E)-O-methyl-oxime;
1-[2-Methyl-8-(2,4,6-trimethyl-phenyl)-quinolin-4-yl]-propan-1-one O-methyl-oxime;
(E)-1-[3,6-Dimethyl-2-(2,4,6-trimethyl-phenoxy)-pyridin-4-yl]-propan-1-one O-methyl-oxime;
(Z)-1-[3,6-Dimethyl-2-(2,4,6-trimethyl-phenoxy)-pyridin-4-yl]-propan-1-one O-methyl-oxime;
1-[7-Methyl-1-(2,4,6-trimethyl-phenyl)-1,4-dihydro-2H-pyrimido[4,5-d][1,3]oxazin-5-yl]-propan-1-one (E)-oxime;
1-[7-Methyl-1-(2,4,6-trimethyl-phenyl)-1,4-dihydro-2H-pyrimido[4,5-d][1,3]oxazin-5-yl]-propan-1-one (Z)-oxime;
1-[2,5,6-Trimethyl-7-(2,4,6-trimethyl-phenyl)-7H-pyrrolo[2,3-d]pyrimidin-4-yl]-ethanone (E)-O-methyl-oxime;
1-[2,5,6-Trimethyl-7-(2,4,6-trimethyl-phenyl)-7H-pyrrolo[2,3-d]pyrimidin-4-yl]-ethanone (Z)-O-methyl-oxime;
[2-(4-Chloro-2,6-dimethyl-phenoxy)-3,6-dimethyl-pyridin-4-yl]-pyridin-2-yl-methanone (Z)-oxime;
1-[2-Methyl-8-(2,4,6-trimethyl-phenyl)-quinolin-4-yl]-propan-1-one O-isobutyl-oxime;
[2-Methyl-8-(2,4,6-trimethyl-phenyl)-quinolin-4-yl]-pyridin-2-yl-methanone O-ethyl-oxime;
Propyl-carbamic acid 1-[2-(4-chloro-2,6-dimethyl-phenoxy)-3,6-dimethyl-pyridin-4-yl]-2,2,2-trifluoro-ethyl ester;
Methyl-carbamic acid 1-[3,6-dimethyl-2-(2,4,6-trimethyl-phenoxy)-pyridin-4-yl]-2,2,2-trifluoro-ethyl ester;
Methyl-carbamic acid 1-[3,6-dimethyl-2-(2,4,6-trimethyl-phenoxy)-pyridin-4-yl]-propyl ester;
Methyl-carbamic acid 2,2,2-trifluoro-1-[2-methyl-8-(2,4,6-trimethyl-phenyl)quinolin-4-yl]-ethyl ester;
Methyl-carbamic acid 1-methyl-2-[2,5,6-trimethyl-7-(2,4,6-trimethyl-phenyl)-7H-pyrrolo[2,3-d]pyrimidin-4-ylamino]-butyl ester;
Methyl-carbamic acid 1-[2,5,6-trimethyl-7-(2,4,6-trimethyl-phenyl)-7H-pyrrolo[2,3-d]pyrimidin-4-yl]-propyl ester;
Methyl-carbamic acid 1-[7-methyl-1-(2,4,6-trimethyl-phenyl)-1,4-dihydro-2H-pyrimido[4,5-d][1,3]oxazin-5-yl]-propyl ester;
1-{1-[3,6-Dimethyl-2-(2,4,6-trimethyl-phenoxy)-pyridin-4-yl]-propyl}-3-methyl-urea
Methyl-carbamic acid 2,2,2-trifluoro-1-[7-methyl-1-(2,4,6-trimethyl-phenyl)-1,4-dihydro-2H-pyrimido[4,5-d][1,3]oxazin-5-yl]-ethyl ester;
1-Methyl-3-{1-[2-methyl-8-(2,4,6-trimethyl-phenyl)-quinolin-4-yl]-propyl}-urea;
N-{Thiazol-2-yl-[2,5,6-trimethyl-7-(2,4,6-trimethyl-phenyl)-7H-pyrrolo[2,3-d]pyrimidin-4-yl]-methyl}-acetamide;
1-Methyl-3-{thiazol-2-yl-[2,5,6-trimethyl-7-(2,4,6-trimethyl-phenyl)-7H-pyrrolo[2,3-d]pyrimidin-4-yl]methyl}-urea;
(E)-1-[2,5,6-Trimethyl-7-(2,6-dimethyl-4-chloro-phenyl)-7H-pyrrolo[2,3-d]pyrimidin-4-yl]-propan-1-one oxime;
(Z)-1-[2,5,6-Trimethyl-7-(2,6-dimethyl-4-chloro-phenyl)-7H-pyrrolo[2,3-d]pyrimidin-4-yl]-propan-1-one oxime;
(E)-1-[2,5-dimethyl-7-(2,6-dimethyl-4-chloro-phenyl)-7H-pyrrolo[2,3-d]pyrimidin-4-yl]-propan-1-one oxime;
(Z)-1-[2,5-Dimethyl-7-(2,6-dimethyl-4-chloro-phenyl)-7H-pyrrolo[2,3-d]pyrimidin-4-yl]-propan-1-one oxime;
(E)-1-[2,5,6-Trimethyl-7-(2,6-dimethyl-4-methoxy-phenyl)-7H-pyrrolo[2,3-d]pyrimidin-4-yl]-propan-1-one oxime;
(Z)-1-[2,5,6-Trimethyl-7-(2,6-dimethyl-4-methoxy-phenyl)-7H-pyrrolo[2,3-d]pyrimidin-4-yl]-propan-1-one oxime;
(E)-1-[2,5,6-Trimethyl-7-(2-methyl-4-chloro-phenyl)-7H-pyrrolo[2,3-d]pyrimidin-4-yl]-propan-1-one oxime;
(Z)-1-[2,5,6-Trimethyl-7-(2-methyl-4-chloro-phenyl)-7H-pyrrolo[2,3-d]pyrimidin-4-yl]-propan-1-one oxime;
(E)-1-[2,5-dimethyl-7-(2,6-dimethyl-4-methoxy-phenyl)-7H-pyrrolo[2,3-d]pyrimidin-4-yl]-propan-1-one oxime;
(Z)-1-[2,5-dimethyl-7-(2,6-dimethyl-4-methoxy-phenyl)-7H-pyrrolo[2,3-d]pyrimidin4-yl]-propan-1-one oxime;
(E)-1-[2,5-dimethyl-7-(2-methyl-4-chloro-phenyl)-7H-pyrrolo[2,3-d]pyrimidin-4-yl]-propan-1-one oxime;
(Z)-1-[2,5-dimethyl-7-(2-methyl-4-chloro-phenyl)-7H-pyrrolo[2,3-d]pyrimidin-4-yl]-propan-1-one oxime;
(E)-1-[2,5-dimethyl-7-(2,4-dimethoxy-phenyl)-7H-pyrrolo[2,3-d]pyrimidin-4-yl]-propan-1-one oxime;
(Z)-1-[2,5-dimethyl-7-(2,4-dimethoxy-phenyl)-7H-pyrrolo[2,3-d]pyrimidin-4-yl]-propan-1-one oxime;
(E)-1-[2,5-dimethyl-7-(2-methyl-4-methoxy-phenyl)-7H-pyrrolo[2,3-d]pyrimidin-4-yl]-propan-1-one oxime;
(Z)-1-[2,5-dimethyl-7-(2-methyl-4-methoxy-phenyl)-7H-pyrrolo[2,3-d]pyrimidin-4-yl]-propan-1-one oxime;
5-Hydroxy-4-(1-hydroxyimino-propyl)-2,5-dimethyl-7-(2,6-dimethyl-4-chloro-phenyl)-5,7-dihydro-pyrrolo[2,3-d]pyrimidin-6-one;
5-Hydroxy-4-(1-hydroxyimino-propyl)-2,5-dimethyl-7-(2-methyl-4-chloro-phenyl)-5,7-dihydro-pyrrolo[2,3-d]pyrimidin-6-one;
5-Hydroxy-4-(1-hydroxyimino-propyl)-2,5-dimethyl-7-(2,6-dimethyl-4-methoxy-phenyl)-5,7-dihydro-pyrrolo[2,3-d]pyrimidin-6-one;
5-Hydroxy-4-(1-hydroxyimino-propyl)-2,5-dimethyl-7-(2,4-dichloro-phenyl)-5,7-dihydro-pyrrolo[2,3-d]pyrimidin-6-one;
5-Hydroxy-4-(1-hydroxyimino-propyl)-2,5-dimethyl-7-(2,4-dimethoxy-phenyl)-5,7-dihydro-pyrrolo[2,3-d]pyrimidin-6-one;
1-[2-Methyl-8-(2,6-dimethyl-4-chloro-phenyl)-quinolin-4-yl]-propan-1-one (E)-oxime;
1-[2-Methyl-8-(2,6-dimethyl-4-chloro-phenyl)-quinolin-4-yl]-propan-1-one (Z)-oxime;
1-[2-Methyl-8-(2-methyl-4-chloro-phenyl)-quinolin-4-yl]-propan-1-one (E)-oxime;

1-[2-Methyl-8-(2-methyl-4-chloro-phenyl)-quinolin-4-yl]-propan-1-one (Z)-oxime;
1-[2-Methyl-8-(2,6-dimethyl-4-bromo-phenyl)-quinolin-4-yl]-propan-1-one (E)-oxime;
1-[2-Methyl-8-(2,6-dimethyl-4-bromo-phenyl)-quinolin-4-yl]-propan-1-one (Z)-oxime;
1-[2-Methyl-8-(2,6-dimethyl-4-methoxy-phenyl)-quinolin-4-yl]-propan-1-one (E)-oxime;
1-[2-Methyl-8-(2,6-dimethyl-4-methoxy-phenyl)-quinolin-4-yl]-propan-1-one (Z)-oxime;
1-[2-Methyl-8-(2,6-dimethyl-4-trifluoromethoxy-phenyl)-quinolin-4-yl]-propan-1-one (E)-oxime;
1-[2-Methyl-8-(2,6-dimethyl-4-trifluoromethoxy-phenyl)-quinolin-4-yl]-propan-1-one (Z)-oxime;
1-[2-Methyl-8-(2,4-dimethyl-phenyl)-quinolin-4-yl]-propan-1-one (E)-oxime;
1-[2-Methyl-8-(2,4-dimethyl-phenyl)-quinolin-4-yl]-propan-1-one (Z)-oxime;
1-[2-Methyl-8-(2,4-dimethoxy-phenyl)-quinolin-4-yl]-propan-1-one (E)-oxime;
1-[2-Methyl-8-(2,4-dimethoxy-phenyl)-quinolin-4-yl]-propan-1-one (Z)-oxime;
1-[2-Methyl-8-(2,4,6-trimethoxy-phenyl)-quinolin-4-yl]-propan-1-one (E)-oxime;
1-[2-Methyl-8-(2,4,6-trimethoxy-phenyl)-quinolin-4-yl]-propan-1-one (Z)-oxime;
1-[2-Methyl-8-(2,6-dimethyl-4-chloro-phenyl)-quinolin-4-yl]-propan-1-one O-methyl-oxime;
1-[2-Methyl-8-(2,6-dimethyl-4-bromo-phenyl)-quinolin-4-yl]-propan-1-one O-methyl-oxime;
1-[2-Methyl-8-(2,6-dimethyl-4-methoxy-phenyl)-quinolin-4-yl]-propan-1-one O-methyl-oxime;
1-[2-Methyl-8-(2,4,6-trimethoxy-phenyl)-quinolin-4-yl]-propan-1-one O-methyl-oxime;
1-[2-Methyl-8-(2,4-dimethoxy-phenyl)-quinolin-4-yl]-propan-1-one O-methyl-oxime;
1-[2-Methyl-8-(2-trifluomethoxy-4-methoxy-phenyl)-quinolin-4-yl]-propan-1-one O-methyl-oxime;
(E)-1-[3,6-Dimethyl-2-(2,6-dimethyl-4-chloro-phenoxy)-pyridin-4-yl]-propan-1-one O-methyl-oxime;
(Z)-1-[3,6-Dimethyl-2-(2,6-dimethyl-4-chloro-phenoxy)-pyridin-4-yl]-propan-1-one O-methyl-oxime;
(E)-1-[3,6-Dimethyl-2-(2,4,6-trimethoxy-phenoxy)-pyridin-4-yl]-propan-1-one O-methyl-oxime;
(Z)-1-[3,6-Dimethyl-2-(2,4,6-trimethoxy-phenoxy)-pyridin-4-yl]-propan-1-one O-methyl-oxime;
(E)-1-[3,6-Dimethyl-2-(2,6-dimethoxy-4-methyl-phenoxy)-pyridin-4-yl]-propan-1-one O-methyl-oxime;
(Z)-1-[3,6-Dimethyl-2-(2,6-dimethoxy-4-methyl-phenoxy)-pyridin-4-yl]-propan-1-one O-methyl-oxime;
1-[7-Methyl-1-(2,6-dimethyl-4-chloro-phenyl)-1,4-dihydro-2H-pyrimido[4,5-d][1,3]oxazin-5-yl]-propan-1-one (E)-oxime;
1-[7-Methyl-1-(2,6-dimethyl-4-chloro-phenyl)-1,4-dihydro-2H-pyrimido[4,5-d][1,3]oxazin-5-yl]-propan-1-one (Z)-oxime;
1-[7-Methyl-1-(2,6-dimethyl-4-methoxy-phenyl)-1,4-dihydro-2H-pyrimido[4,5-d][1,3]oxazin-5-yl]-propan-1-one (E)-oxime;
1-[7-Methyl-1-(2,6-dimethyl-4-methoxy-phenyl)-1,4-dihydro-2H-pyrimido[4,5-d][1,3]oxazin-5-yl]-propan-1-one (Z)-oxime;
1-[2,5,6-Trimethyl-7-(2,6-dimethyl-4-chloro-phenyl)-7H-pyrrolo[2,3-d]pyrimidin-4-yl]-ethanone (E)-O-methyl-oxime;
1-[2,5,6-Trimethyl-7-(2,6-dimethyl-4-chloro-phenyl)-7H-pyrrolo[2,3-d]pyrimidin-4-yl]-ethanone (Z)-O-methyl-oxime;
1-[2,5,6-Trimethyl-7-(2,6-dimethyl-4-methoxy-phenyl)-7H-pyrrolo[2,3-d]pyrimidin-4-yl]-ethanone (E)-O-methyl-oxime;
1-[2,5,6-Trimethyl-7-(2,6-dimethyl-4-methoxy-phenyl)-7H-pyrrolo[2,3-d]pyrimidin-4-yl]-ethanone (Z)-O-methyl-oxime;
1-[2,5,6-Trimethyl-7-(2,4-dimethoxy-phenyl)-7H-pyrrolo[2,3-d]pyrimidin-4-yl]-ethanone (E)-O-methyl-oxime;
1-[2,5,6-Trimethyl-7-(2,4-dimethoxy-phenyl)-7H-pyrrolo[2,3-d]pyrimidin-4-yl]-ethanone (Z)-O-methyl-oxime;
1-[2,5,6-Trimethyl-7-(2,4-dichloro-phenyl)-7H-pyrrolo[2,3-d]pyrimidin-4-yl]-ethanone (E)-O-methyl-oxime;
1-[2,5,6-Trimethyl-7-(2,4-dichloro-phenyl)-7H-pyrrolo[2,3-d]pyrimidin-4-yl]-ethanone (Z)-O-methyl-oxime;
[2-(4-Chloro-2,6-dimethyl-phenoxy)-3,6-dimethyl-pyridin-4-yl]-pyridin-2-yl-methanone (Z)-oxime;
1-[2-Methyl-8-(2,6-dimethyl-4-chloro-phenyl)-quinolin-4-yl]-propan-1-one O-isobutyl-oxime;
(Z)-1-[2,5,6-Trimethyl-7-(2,6-dimethyl-4-chloro-phenyl)-7H-pyrrolo[2,3-d]pyrimidin-4-yl]-propan-1-one oxime;
[2-(4-methoxy-2,6-dimethyl-phenoxy)-3,6-dimethyl-pyridin-4-yl]-pyridin-2-yl-methanone (Z)-oxime;
1-[2-Methyl-8-(2,6-dimethyl-4-methoxy-phenyl)-quinolin-4-yl]-propan-1-one O-isobutyl-oxime;
(Z)-1-[2,5,6-Trimethyl-7-(2,6-dimethyl-4-methoxy-phenyl)-7H-pyrrolo[2,3-d]pyrimidin-4-yl]-propan-1-one oxime;
5-Hydroxy-4-(1-hydroxyimino-propyl)-2,5-dimethyl-7-(2,6-dimethyl-4-chloro-phenyl)-5,7-dihydro-pyrrolo[2,3-d]pyrimidin-6-one;
5-Hydroxy-4-(1-hydroxyimino-propyl)-2,5-dimethyl-7-(2,4-dimethoxy-phenyl)-5,7-dihydro-pyrrolo[2,3-d]pyrimidin-6-one;
5-Hydroxy-4-(1-hydroxyimino-propyl)-2,5-dimethyl-7-(2,6-dimethyl-4-methoxy-phenyl)-5,7-dihydro-pyrrolo[2,3-d]pyrimidin-6-one;
5-Hydroxy-4-(1-hydroxyimino-propyl)-2,5-dimethyl-7-(2,4,6-trimethoxy-phenyl)-5,7-dihydro-pyrrolo[2,3-d]pyrimidin-6-one;
1-[2-Methyl-8-(2,6-dimethyl-4-chloro-phenyl)-quinolin-4-yl]-propan-1-one (E)-oxime;
1-[2-Methyl-8-(2,6-dimethyl-4-chloro-phenyl)-quinolin-4-yl]-propan-1-one (Z)-oxime;
1-[2-Methyl-8-(2,6-dimethyl-4-chloro-phenyl)-quinolin-4-yl]-propan-1-one (E)-O-methyl-oxime;
1-[2-Methyl-8-(2,6-dimethyl-4-methoxy-phenyl)-quinolin-4-yl]-propan-1-one (E)-oxime;
1-[2-Methyl-8-(2,6-dimethyl-4-methoxy-phenyl)-quinolin-4-yl]-propan-1-one (Z)-oxime;
1-[2-Methyl-8-(2,6-dimethyl-4-methoxy-phenyl)-quinolin-4-yl]-propan-1-one (E)-O-methyl-oxime;
1-[2-Methyl-8-(2,6-dimethyl-4-chloro-phenyl)-quinolin-4-yl]-propan-1-one O-methyl-oxime;
1-[2-Methyl-8-(2,6-dimethyl-4-methoxy-phenyl)-quinolin-4-yl]-propan-1-one O-methyl-oxime;
(E)-1-[3,6-Dimethyl-2-(2,6-dimethyl-4-chloro-phenoxy)-pyridin-4-yl]-propan-1-one O-methyl-oxime;
(Z)-1-[3,6-Dimethyl-2-(2,6-dimethyl-4-chloro-phenoxy)-pyridin-4-yl]-propan-1-one O-methyl-oxime;
1-[7-Methyl-1-(2,6-dimethyl-4-chloro-phenyl)-1,4-dihydro-2H-pyrimido[4,5-d][1,3]oxazin-5-yl]-propan-1-one (E)-oxime;
1-[7-Methyl-1-(2,6-dimethyl-4-chloro-phenyl)-1,4-dihydro-2H-pyrimido[4,5-d][1,3]oxazin-5-yl]-propan-1-one (Z)-oxime;
(E)-1-[3,6-Dimethyl-2-(2,6-dimethyl-4-methoxy-phenoxy)-pyridin-4-yl]-propan-1-one O-methyl-oxime;

(Z)-1-[3,6-Dimethyl-2-(2,6-dimethyl-4-methoxy-phenoxy)-pyridin-4-yl]-propan-1-one O-methyl-oxime;
1-[7-Methyl-1-(2,6-dimethyl-4-methoxy-phenyl)-1,4-dihydro-2H-pyrimido[4,5-d][1,3]oxazin-5-yl]-propan-1-one (E)-oxime;
1-[7-Methyl-1-(2,6-dimethyl-4-methoxy-phenyl)-1,4-dihydro-2H-pyrimido[4,5-d][1,3]oxazin-5-yl]-propan-1-one (Z)-oxime;
1-[2,5,6-Trimethyl-7-(2,6-dimethyl-4-chloro-phenyl)-7H-pyrrolo[2,3-d]pyrimidin-4-yl]-ethanone (E)-O-methyl-oxime;
1-[2,5,6-Trimethyl-7-(2,6-dimethyl-4-chloro-phenyl)-7H-pyrrolo[2,3-d]pyrimidin-4-yl]-ethanone (Z)-O-methyl-oxime;
[2-(4-Chloro-2,6-dimethyl-phenoxy)-3,6-dimethyl-pyridin-4-yl]-pyridin-2-yl-methanone (Z)-oxime;
1-[2-Methyl-8-(2,6-dimethyl-4-chloro-phenyl)-quinolin-4-yl]-propan-1-one O-isobutyl-oxime;
[2-Methyl-8-(2,6-dimethyl-4-chloro-phenyl)-quinolin-4-yl]-pyridin-2-yl-methanone O-ethyl-oxime;
1-[2,5,6-Trimethyl-7-(2,6-dimethyl-4-methoxy-phenyl)-7H-pyrrolo[2,3-d]pyrimidin-4-yl]-ethanone (E)-O-methyl-oxime;
1-[2,5,6-Trimethyl-7-(2,6-dimethyl-4-methoxy-phenyl)-7H-pyrrolo[2,3-d]pyrimidin-4-yl]-ethanone (Z)-O-methyl-oxime;
[2-(4-methoxy-2,6-dimethyl-phenoxy)-3,6-dimethyl-pyridin-4-yl]-pyridin-2-yl-methanone (Z)-oxime;
1-[2-Methyl-8-(2,6-dimethyl-4-methoxy-phenyl)-quinolin-4-yl]-propan-1-one O-isobutyl-oxime;
[2-Methyl-8-(2,6-dimethyl-4-methoxy-phenyl)-quinolin-4-yl]-pyridin-2-yl-methanone O-ethyl-oxime,
Propyl-carbamic acid 1-[2-(4-methoxy-2,6-dimethyl-phenoxy)-3,6-dimethyl-pyridin-4-yl]-2,2,2-trifluoro-ethyl ester;
Methyl-carbamic acid 1-[3,6-dimethyl-2-(2,6-dimethyl-4-chloro-phenoxy)-pyridin-4-yl]-2,2,2-trifluoro-ethyl ester;
Methyl-carbamic acid 1-[3,6-dimethyl-2-(2,6-dimethyl-4-chloro-phenoxy)-pyridin-4-yl]-propyl ester;
Methyl-carbamic acid 2,2,2-trifluoro-1-[2-methyl-8-(2,6-dimethyl-4-chloro-phenyl)-quinolin-4-yl]-ethyl ester;
Methyl-carbamic acid 1-methyl-2-[2,5,6-trimethyl-7-(2,6-dimethyl-4-chloro-phenyl)-7H-pyrrolo[2,3-d]pyrimidin-4-ylamino]-butyl ester;
Methyl-carbamic acid 1-[2,5,6-trimethyl-7-(2,6-dimethyl-4-chloro-phenyl)-7H-pyrrolo[2,3-d]pyrimidin-4-yl]-propyl ester;
Methyl-carbamic acid 1-[7-methyl-1-2,6-dimethyl-4-chloro-phenyl)-1,4-dihydro-2H-pyrimido[4,5-d][1,3]oxazin-5-yl]-propyl ester;
1-{1-[3,6-Dimethyl-2-(2,6-dimethyl-4-chloro-phenoxy)-pyridin-4-yl]-propyl}-3-methyl-urea;
Methyl-carbamic acid 2,2,2-trifluoro-1-[7-methyl-1-(2,6-dimethyl-4-chloro-phenyl)-1,4-dihydro-2H-pyrimido[4,5-d][1,3]oxazin-5-yl]-ethyl ester;
1-Methyl-3-{1-[2-methyl-8-(2,6-dimethyl-4-chloro-phenyl)-quinolin-4-yl]-propyl}-urea;
N-{Thiazol-2-yl-[2,5,6-trimethyl-7-(2,6-dimethyl-4-chloro-phenyl)-7H-pyrrolo[2,3-d]pyrimidin-4-yl]-methyl}-acetamide;
1-Methyl-3-{thiazol-2-yl-[2,5,6-trimethyl-7-(2,6-dimethyl-4-chloro-phenyl)-7H-pyrrolo[2,3-d]pyrimidin-4-yl]-methyl}-urea;
Methyl-carbamic acid 1-[3,6-dimethyl-2-(2,6-dimethyl-4-methoxy-phenoxy)-pyridin-4-yl]-2,2,2-trifluoro-ethyl ester;
Methyl-carbamic acid 1-[3,6-dimethyl-2-(2,6-dimethyl-4-methoxy-phenoxy)-pyridin-4-yl]-propyl ester;
Methyl-carbamic acid 2,2,2-trifluoro-1-[2-methyl-8-(2,6-dimethyl-4-methoxy-phenyl)-quinolin-4-yl]-ethyl ester;
Methyl-carbamic acid 1-methyl-2-[2,5,6-trimethyl-7-(2,6-dimethyl-4-methoxy-phenyl)-7H-pyrrolo[2,3-d]pyrimidin-4-ylamino]-butyl ester;
Methyl-carbamic acid 1-[2,5,6-trimethyl-7-(2,6-dimethyl-4-methoxy-phenyl)-7H-pyrrolo[2,3-d]pyrimidin-4-yl]-propyl ester;
Methyl-carbamic acid 1-[7-methyl-1-(2,6-dimethyl-4-methoxy-phenyl)-1,4-dihydro-2H-pyrimido[4,5-d][1,3]oxazin-5-yl]-propyl ester;
1-{1-[3,6-Dimethyl-2-(2,6-dimethyl-4-methoxy-phenoxy)-pyridin-4-yl]-propyl}-3-methyl-urea;
Methyl-carbamic acid 2,2,2-trifluoro-1-[7-methyl-1-(2,6-dimethyl-4-methoxy-phenyl)-1,4-dihydro-2H-pyrimido[4,5-d][1,3]oxazin-5-yl]-ethyl ester;
1-Methyl-3-{1-[2-methyl-8-(2,6-dimethyl-4-methoxy-phenyl)-quinolin-4-yl]-propyl}-urea;
N-{Thiazol-2-yl-[2,5,6-trimethyl-7-(2,6-dimethyl-4-methoxy-phenyl)-7H-pyrrolo[2,3-d]pyrimidin-4-yl]-methyl}-acetamide; and
1-Methyl-3-{thiazol-2-yl-[2,5,6-trimethyl-7-(2,6-dimethyl-4-methoxy-phenyl)-7H-pyrrolo[2,3-d]pyrimidin-4-yl]-methyl}-urea.

Preferred compounds listed above are:

(E)-1-[2,5,6-Trimethyl-7-(2,4,6-trimethyl-phenyl)-7H-pyrrolo[2,3-d]pyrimidin-4-yl]-propan-1-one oxime;
(Z)-1-[2,5,6-Trimethyl-7-(2,4,6-trimethyl-phenyl)-7H-pyrrolo[2,3-d]pyrimidin-4-yl]-propan-1-one oxime;
1-[2-Methyl-8-(2,4,6-trimethyl-phenyl)-quinolin-4-yl]-propan-1-one (E)-oxime;
1-[2-Methyl-8-(2,4,6-trimethyl-phenyl)-quinolin-4-yl]-propan-1-one (Z)-oxime;
(E)1-[2-Methyl-8-(2,4,6-trimethyl-phenyl)-quinolin-4-yl]-propan-1-one-O-methyl-oxime;
(Z)-1-[2-Methyl-8-(2,4,6-trimethyl-phenyl)-quinolin-4-yl]-propan-1-one O-methyl-oxime;
(E)-1-[3,6-Dimethyl-2-(2,4,6-trimethyl-phenoxy)-pyridin-4-yl]-propan-1-one oxime;
(Z)-1-[3,6-Dimethyl-2-(2,4,6-trimethyl-phenoxy)-pyridin-4-yl]-propan-1-one oxime;
(E)-1-[3,6-Dimethyl-2-(2,4,6-trimethyl-phenoxy)-pyridin-4-yl]-propan-1-one O-methyl-oxime;
(Z)-1-[3,6-Dimethyl-2-(2,4,6-trimethyl-phenoxy)-pyridin-4-yl]-propan-1-one O-methyl-oxime;
1-[7-Methyl-1-(2,4,6-trimethyl-phenyl)-1,4-dihydro-2H-pyrimido[4,5-d][1,3]oxazin-5-yl]-propan-1-one (E)-oxime;
1-[7-Methyl-1-(2,4,6-trimethyl-phenyl)-1,4-dihydro-2H-pyrimido[4,5-d][1,3]oxazin-5-yl]-propan-1-one (Z)-oxime;
(E) and (Z)-[2-(4Chloro-2,6-dimethyl-phenoxy)-3,6-dimethyl-pyridin-4-yl]-pyridin-2-yl-methanone (Z)-oxime;
1-[2-Methyl-8-(2,4,6-trimethyl-phenyl)-quinolin-4-yl]-propan-1-one O-isobutyl-oxime;
(E) and (Z)-1-[2,5,6-Trimethyl-7-(2,4,6-trimethyl-phenyl)-7H-pyrrolo[2,3-d]pyrimidin-4-yl]-ethanone (Z)-O-methyl-oxime;
Propyl-carbamic acid 1-[2-(4-chloro-2,6-dimethyl-phenoxy)-3,6-dimethyl-pyridin-4-yl]-2,2,2-trifluoro-ethyl ester;
Methyl-carbamic acid 1-[3,6-dimethyl-2-(2,4,6-trimethyl-phenoxy)-pyridin-4-yl]-2,2,2-trifluoro-ethyl ester;
Methyl-carbamic acid 1-[3,6-dimethyl-2-(2,4,6-trimethyl-phenoxy)-pyridin-4-yl]-propyl ester;

Methyl-carbamic acid 2,2,2-trifluoro-1-[2-methyl-8-(2,4,6-trimethyl-phenyl)-quinolin-4-yl]-ethyl ester;
Methyl-carbamic acid 1-methyl-2-[2,5,6-trimethyl-7-(2,4,6-trimethyl-phenyl)-7H-pyrrolo[2,3-d]pyrimidin-4-ylamino]-butyl ester;
Methyl-carbamic acid 1-[2,5,6-trimethyl-7-(2,4,6-trimethyl-phenyl)-7H-pyrrolo[2,3-d]pyrimidin-4-yl]-propyl ester;
Methyl-carbamic acid 1-[7-methyl-1-(2,4,6-trimethyl-phenyl)-1,4-dihydro-2H-pyrimido[4,5-d][1,3]oxazin-5-yl]-propyl ester;
1-{1-[3,6-Dimethyl-2-(2,4,6-trimethyl-phenoxy)-pyridin-4yl]-propyl}-3-methyl-urea
Methyl-carbamic acid 2,2,2-trifluoro-1-[7-methyl-1-(2,4,6-trimethyl-phenyl)-1,4-dihydro-2H-pyrimido[4,5-d][1,3]oxazin-5-yl]-ethyl ester;
1-Methyl-3-{1-[2-methyl-8-(2,4,6-trimethyl-phenyl)-quinolin-4-yl]-propyl}-urea;
N-{Thiazol-2-yl-[2,5,6-trimethyl-7-(2,4,6-trimethyl-phenyl)-7H-pyrrolo[2,3-d]pyrimidin-4-yl]-methyl}-acetamide; and
1-Methyl-3-{thiazol-2-yl-[2,5,6-trimethyl-7-(2,4,6-trimethyl-phenyl)-7H-pyrrolo[2,3-d]pyrimidin-4-yl]-methyl}-urea.

The invention also relates to a pharmaceutical composition for the treatment of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and post-partum depression; dysthemia; bipolar disorders; schizophrenia; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies and addictions (e.g., dependencies on alcohol, nicotine, cocaine, heroin, benzodiazepines, or other drugs); drug and alcohol withdrawal symptoms; stress-induced psychotic episodes; euthyroid sick syndrome; syndrome of inappropriate antidiuretic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type: multiinfarct dementia; amyotrophic lateral sclerosis; hypertension; tachycardia; congestive heart failure; osteoporosis; premature birth; hypoglycemia; disorders that can be treated by altering circadian rhythm (e.g. time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia and abnormal circadian rhythm associated with chronic administration and withdrawal of antidepressant agents); migraine or non-migraine headache; emesis (e.g. emesis induced by pregnancy, vestibular disorder, post-operative sickness, gastrointestinal obstruction, reduced gastrointestinal motility, visceral pain, migraine, change in intercranial pressure, chemotherapy, radiation, toxins, and opioid analgesics); or syndrome X (also known as metabolic syndrome, plurimetabolic syndrome or insulin resistance syndrome, encompassing a complex of disturbances of carbohydrate and fat metabolism characterized by obesity, dyslipoproteinemia (low HDL and high LDL, VLDL and triglycerides), hyperinsulinemia, insulin resistance, glucose intolerance and hypertension); in a mammal, including a human, comprising an amount of a compound of Formulas I–V, or a pharmaceutically acceptable salt thereof, that is effective in the treatment of such disorder, and a pharmaceutically acceptable carrier.

The invention also relates to a method for the treatment of (a) a disorder the treatment of which can be effected or facilitated by antagonizing CRF, including but not limited to disorders induced or facilitated by CRF, or (b) a disorder selected from inflammatory disorders such as rheumatoid arthritis and osteoarthritis, pain, asthma, psoriasis and allergies; generalized anxiety disorder; panic; phobias; obsessive-compulsive disorder; post-traumatic stress disorder, sleep disorders induced by stress; pain perception such as fibromyalgia; mood disorders such as depression, including major depression, single episode depression, recurrent depression, child abuse induced depression, mood disorders associated with premenstrual syndrome, and post-partum depression; dysthemia; bipolar disorders; schizophrenia; cyclothymia; chronic fatigue syndrome; stress-induced headache; cancer; irritable bowel syndrome; Crohn's disease; spastic colon; post operative ileus; ulcer; diarrhea; stress-induced fever; human immunodeficiency virus (HIV) infections; neurodegenerative diseases such as Alzheimer's disease, Parkinson's disease and Huntington's disease; gastrointestinal diseases; eating disorders such as anorexia and bulimia nervosa; hemorrhagic stress; stress-induced psychotic episodes; euthyroid sick syndrome; syndrome of inappropriate antidiuretic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, nicotine, cocaine, heroin, benzodiazepines, or other drugs); drug and alcohol withdrawal symptoms; hypertension; tachycardia; congestive heart failure; osteoporosis; premature birth; and hypoglycemia; disorders that can be treated by altering circadian rhythm (e.g. time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia and abnormal circadian rhythm associated with chronic administration and withdrawal of antidepressant agents); migraine or non-migraine headache; emesis (e.g. emesis induced by pregnancy, vestibular disorder, postoperative sickness, gastrointestinal obstruction, reduced gastrointestinal motility, visceral pain, migraine, change in intercranial pressure, chemotherapy, radiation, toxins, and opioid analgesics); or syndrome X; in a mammal, including a human, comprising administering to a subject in need of said treatment an amount of a compound of Formulas I–V, or a pharmaceutically acceptable salt, or prodrug thereof, that is effective in treating such disorder, and a pharmaceutically acceptable carrier.

This structures of Formulas I–V encompass all optical isomers, and other stereoisomers, tautomers, and geometric isomers of these compounds. When such compounds contain one or more chiral centers, it is understood that the invention includes the racemic mixtures as well as all individual enanbomers and diastereomers of such compounds, and mixtures thereof. Many geometric isomers of olefin, C=N double bonds, and the like can also be present in the compounds, and all such stable isomers are encompassed by in the present invention. The compounds may be isolated in optically active or racemic or mixture forms. It is well known in the art how to prepare optically active forms, such as by resolution of racemic forms or by synthesis from optically active starting materials, or by synthesis and separation of the diasteroismeric derivatives which can be derived from reacting the racemic forms with a chiral agent, followed by regenerating the enantiomeric forms. All chiral (enantiomeric and diastereomeric) and racemic forms and all geometric isomeric forms of the compounds are intended, unless the specific stereochemistry or isomer form is specifically indicated.

The structures of Formulas I–V are also understood to refer to, and the invention to encompass, all tautomers thereof. The invention also encompasses mixtures of compounds of Formulas I–V.

The invention also encompasses prodrugs of the compounds of the Formulas I–V. A "Prodrug" is considered to be any covalently bonded carrier which releases the active parent drug of Formulas I–V in vivo when such prodrug is administered to a mammalian subject. Prodrugs of the compounds of the invention are prepared, e.g., by modifying a functional group present in the compounds in such a way that the modifications are cleaved to form the parent compounds. Prodrugs include, without limitation, compounds wherein hydroxy, amine, or carboxyl groups are bonded to any group that, when administered to a mammalian subject, are cleaved to form a free hydroxy, amine or carboxyl, respectively. It is well known in the art how to prepare such prodrugs which include, but are not limited to, acetate, formate, and benzoate derivatives of alcohol and amine functional groups in the compounds of Formulas I–V, and the like. Prodrugs can also, for example, comprise an amino acid residue, or a polypeptide chain of two or more (e.g., two, three or four) amino acid residues which are covalently joined through peptide bonds to free amino, hydroxy or carboxylic acid groups of compounds of Formulas I–V. The amino acid residues include the 20 naturally occurring amino acids commonly designated by three letter symbols and also are selected from 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs are also understood to include carbonates, carbamates, amides and alkyl esters which are covalently bonded to the above substituents of Formulas I–V through the carbonyl carbon prodrug side chain. The prodrugs then hydrolyze to the parent compound in the body after administration.

The compounds of this invention also include compounds that are identical to those described above but for the fact that one or more hydrogen, nitrogen or carbon atoms are replaced by isotopes thereof (e.g., deuterium, tritium or carbon-14 isotopes). Such compounds are useful, e.g., as research and diagnostic tools in metabolism pharmokinetic studies and in binding assays.

DETAILED DESCRIPTION OF THE INVENTION

All patents, patent publications, and literature references cited herein are hereby incorporated by reference.

Reference herein to "alkyl" is intended to include both branched and straight-chain alkyl. "Aryl" is an aromatic hydrocarbon ring and "heteroaryl" is a heteroaromatic ring.

Common abbreviations have the following meanings: Me is methyl, Et is ethyl, Pr is propyl, and Bu is butyl. The prefix "n" refers to a straight chain alkyl. The prefix "c" refers to a cycloalkyl. The prefix "S" or "R" refers to the (S) or (R) enantiomer, respectively. The prefixes "E" and "Z" refer to trans and cis isomers, respectively. It is understood in the Formulae described herein that at least two carbons or atoms must be present in an alkyl group for a double or triple bond to be present in the group.

"Treatment" is used herein to refer to the alleviation, inhibition, or prevention of a disorder or condition, including but not limited to alleviation, inhibition, or prevention of one or more symptoms of the disorder or condition, or of the onset of the disorder or condition.

Methods of preparing compounds of the invention are described below. In the reaction schemes shown, "Ring" refers to the portion of the compounds of Formulas I–V that is attached to the B group.

Compounds of Formulas I to V wherein B is —C(R²)(=N—Y¹R¹) may be prepared according to Scheme I by reacting the corresponding carbonyl derivative (Formula XXIV), i.e., wherein the compound contains a C=O group at the position where the =N—Y¹R¹ portion of the B group is to be present, with a compound of the Formula NH₂—Y¹R¹. The reaction is conducted in an appropriate solvent or a mixture of solvents selected from $C_1$–$C_6$ alcohol, methylene chloride, DMSO, THF, pyridine, trimethylpyridine, DMF, dichloroethane, acetone, acetonitrile, 1-methyl-2-pyrrolidinone with or without a base selected from potassium carbonate, sodium carbonate, tri-($C_1$–$C_4$ alkyl)amine, pyridine, and dimethylaminopyridine at a temperature of between 0° C. to 150° C., preferably between 0° C. to 60° C.

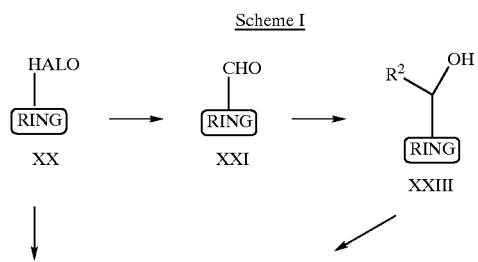

Scheme I

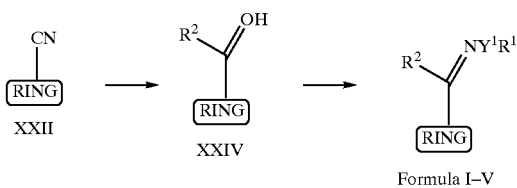

Formula I–V

The compound containing the corresponding carbonyl derivative (Formula XXIV) can be obtained, e.g., by following the methods described in WO 94/13677 (published Jun. 23, 1994), WO 94/13676 (published Jun. 23, 1994), WO95/33750 (published Dec. 14, 1995), WO 95/34563 (published Dec. 21, 1995), EP 778277 (published Jun. 11, 1997), WO 98/05661 (published Feb. 12, 1998), WO 98/08847 (published Mar. 5, 1998), and WO 98/08846 (published Mar. 5, 1998), and briefly described below, according to Scheme I. In general, compounds of Formula XXII (the corresponding cyano derivative) may be prepared by reacting the compounds of Formula XX (the corresponding halo derivative) with potassium cyanide, copper cyanide or sodium cyanide, or di-($C_1$-$C_4$alkyl)aluminum cyanide in an appropriate solvent such as dimethylsulfoxide, DMF, toluene, or xylene at a temperature from room temperature to 180° C., preferably 60° C. to 150° C., with or without Pd(II)OAc or Pd(0)(PPh$_3$)$_4$.

Compounds of Formula XXI (the corresponding formyl (CHO) derivative) may be prepared by reacting compounds of Formula XX wherein HALO is Cl, Br, or I, preferably Br or I, with an organolithium reagent (e.g., t-BuLi, s-BuLi, or n-BuLi) in an appropriate solvent (such as THF, dioxane, ether, benzene, or methylene chloride) at a temperature of from –120° C. to room temperature, preferably at –110° C. to –60° C., followed by quenching with an appropriate electrophile, such as DMF or ethyl formate. Conversion of compounds of Formula XXI to compounds of Formula XXIII, and then XXIV may be accomplished using a conventional organometalics addition reaction (such as, but not limited to, a Grignard reaction (using $R^2$Mg-halo) or an organometallics addition (using $R^2$Li, ($R^2$)$_3$Al)), followed by oxidation of the corresponding alcohol to ketone using standard methods known in art The carbonyl derivative (XXIV) can also be prepared from a compound of Formula XXII using a standard organometallics addition reaction (such as but not limited to Grignard addition (using $R^2$Mg-halo) or organolithium addition (using ($R^2$Li)). The compound of Formula XXIII may also be prepared by halogen-metal exchange of a compound of Formula XX, followed by quenching with a compound of the Formula $R^2$CHO using conventional procedures known in the art.

Compounds of Formulas I to V wherein B is —$Y^3C(R^2)$ (=$NY^1R^1$), —$NR^{16}R^2$, —$NHCR^{16}R^2$, —$SCHR^{16}R^2$, —$CHR^{16}R^2$, —$C(OH)R^{16}R^2$, —$CHR^{16}(OR^1)$, —$C(F)$ $R^{16}R^2$, —$C(OMe)R^{16}R^2$, —$CR^{16}(=CR^2R^1)$, —$CHR^{16}$ ($NR^1$), or =$C(R^2)(R^{16})$ may be prepared by reacting the corresponding carbonyl derivative, i.e., a compound containing a C=O group at the position where the =$N—Y^1R^1$ group is present in the B group of Formulas I–V, with a compound of the Formula $NH_2—Y^1R^1$. The reaction is conducted in an appropriate solvent selected from $C_1$–$C_6$ alcohol, methylene chloride, DMSO, THF, pyridine, trimethylpyridine, DMF, dichloroethane, acetone, acetonitrile, and 1-methyl-2-pyrrolidinone with or without a base selected from potassium carbonate, sodium carbonate, tri-($C_1$–$C_4$ alkyl)amine, pyridine, and dimethylaminopyridine at a temperature between 0° C. to 150° C., preferably between 0° C. to 60° C. Syntheses of the corresponding carbonyl compounds are described in WO 94/13677 (published Jun. 23, 1994), WO 94/13676 (published Jun. 23, 1994), WO95/33750 (published Dec. 14, 1995), WO 95/34563 (published Dec. 21, 1995), EP 778277 (published Jun. 11, 1997), WO 98/05661 (published Feb. 12, 1998), WO 98/08847 (published Mar. 5, 1998), and WO 98/08846 (published Mar. 5, 1998). These patent publications also describe starting materials employed in the syntheses described below.

Compounds of Formulas I to V wherein B is —$C(R^2)$ ($NR^{14}C(=X^2)NR^1H$), may be prepared by reacting compounds corresponding to those of Formulas I to V but having a group of the formula —$C(R^2)(NHR^{14})$ corresponding to the position of the B group with $R^1N=C=X^2$ in an appropriate solvent selected from dichloroethane, chloroform, methylene chloride, DMF, acetonitrile, benzene, toluene, THF, and dioxane, at a temperature from 0° C. to reflux, preferably at room temperature to 100° C. N-alkylation of compounds of Formulas I to V wherein B is —$C(R^2)(NR^{14}C(=X^2)NR^1H)$, with $R^{15}$—$X^3$ (where $X^3$ is a leaving group, such as a halo, mesylate, or tosylate) using standard methods known in the art, provides compounds of Formulas I to V wherein B is $C(R^2)(NR^{14}C(=X^2)NR^1R^{15})$.

Compounds of Formulas I to V wherein B is —$C(R^2)$ ($OC(=X^2)NR^1H$), may be prepared by reacting compounds corresponding to those of Formulas I to V, but having a group of the formula —$C(R^2)(OH)$ corresponding to the position of the B group of formula I to V with a compound of the Formula $R^1N=C=X^2$. The reaction is conducted with or without a base selected from dimethylaminopyridine, triethylamine, potassium carbonate, sodium hydride, and potassium t-butoxide in an appropriate solvent selected from dichloroethane, chloroform, methylene chloride, DMF, acetonitrile, benzene, toluene, THF, and dioxane, at a temperature from 0° C. to reflux, preferably at room temperature to reflux. N-alkylaton of compounds in the Formulas I to V wherein B is $C(R^2)(OC(=X^2)NR^1H)$ with $R^{15}$—$X^3$ (where $X^3$ is a leaving group, such as a halo, mesylate, or tosylate) using methods known in the art provides compounds of Formulas I to V wherein B is —$C(R^2)(OC(=X^2)NR^1R^{15})$.

Compounds of Formulas I to V wherein B is —$C(R^2)$ ($NR^{14}C(=X^2)R^{15}$), may be prepared by reacting compounds corresponding to those of Formulas I to V, but having a group of the formula —$C(R^2)(NHR^{14})$ corresponding to the position of the B group of formula I to V with $R^{15}C(=X^2)$—$L^2$ (where $L^2$ is a leaving group selected from halo, mesylate, and tosylate) or [$R^{15}C(=X^2)$]$_2$O. The reaction is conducted with or without a base selected from dimethylaminopyridine, triethylamine, potassium carbonate, sodium hydride, and potassium t-butoxide in an appropriate solvent selected from dichloroethane, chloroform, methylene chloride, DMF, DMSO, acetonitrile, benzene, toluene, THF, and dioxane, at a temperature from 0° C. to reflux, preferably at room temperature to reflux.

Compounds of Formulas I to V wherein B is $Y^3$—C ($Y^2R^2$)(=$NHR^1$), may be prepared according to Scheme II by reacting compounds of Formulas XVI, with $Y^2HR^2$ followed by N-alkylation with $R^1$—$L^3$ (where $L^3$ is a leaving group such as halo, tosylate, mesylate, or triflate using procedures known in the art, including use of an appropriate solvent or mixture of solvents (such as alkyl alcohol, acetonitrile, acetone, DMSO, DMF, methylene chloride, chloroform, dichloroethane, THF, water, sulfolane, acetamide, ethyl acetate, benzene, toluene, or pyridine) in the presence or absence of a base (such as sodium hydride, or organometallic lithium or sodium base such as LDA, n-BuLi, or sodium/lithium bis(trimethylsilylamide), potassium hydride, dimethylaminopyridine, triethylamine, potassium carbonate, sodium hydride, or potassium t-butoxide) at a temperature between −78° C. to 200° C., preferably at reflux, using conditions known in the art. Compounds of formula XVI may be prepared by reacting XVIII with cyanogen halide using known methods (see Chem. Ber., 1908, 41:524; Acta Chem. Scand.: 1993, 47:974–978; J. Amer. Chem. Soc., 1996, 118:6868–6872; Chem. Ber., 1968, 101:3185–3200; Chem. Ber., 1964, 97:3027–3035; Chem. Ber., 1966, 99:958–975; Chem. Ber., 1968, 101:3185–3200; Chem. Ber., 1964, 97:3027–3035; Chem. Ber., 1965, 98:3286–3296; Chem. Ber., 1968, 101:3185–3200; Hoppe-Seyler's Z. Physiol. Chem., 1926, 155:43591; Chem. Ber., 1978, 111:320–334).

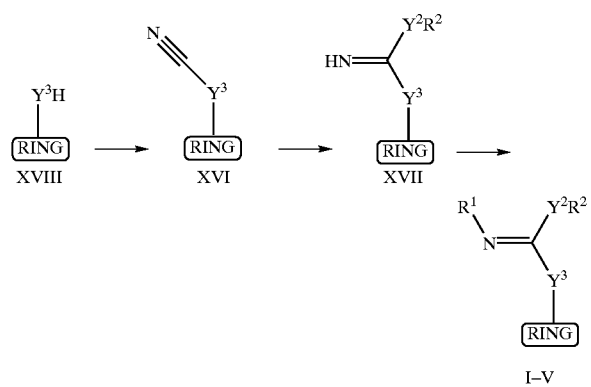

It is understood that general organic chemistry methodology is applied, where required, to alter the steps of the reactions described above depending on the feasibility of the reaction. This includes, e.g., using an appropriate protecting group, or reducing an ester group to the corresponding $C_1$–$C_4$ alkyl group, as required at any stage of synthesis.

The acid addition salts of Formulas I–V can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The compounds of Formulae I–V and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions, oils (e.g., peanut oil, sesame oil) and various organic solvents. The pharmaceutical compositions formed by combining the active compounds of the invention and pharmaceutically acceptable carriers can then be readily administered in a variety of dosage forms such as tablets, powders, lozenges, emulsions, oil soft gels, syrups, injectable solutions, spray-dried formulations, transdermal or transmucosal patches, inhalable formulations and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talk are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the active compounds of this invention will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastro-intestinal diseases, anorexia nervosa, hemorrhagic stress and drug and alcohol withdrawal symptoms will generally range from about 0.1 to about 50 mg/kg body weight of the patient to be treated.

Methods that may be used to determine the CRF antagonist activity of the active compounds of this invention and their pharmaceutically acceptable salts are described in Endocrinology, 116, 1653–1659 (1985) and Peptides, 10, 179–188 (1985). The binding activities for compounds of the invention, expressed as $IC_{50}$ values, generally range from about 0.5 nanomolar to about 32 micromolar.

The CRF antagonist may be used alone or in combination with other agents for the treatment of CRF related diseases.

For example, where the compound of the invention is used to treat cardiovascular disease, another compound for treating cardiovascular disease can also be administered. The second compound can be, for example, adenosine, alteplase, amiodarone, anagrelide, ardeparin, argatroban, atenolol, atorvastatin, benazepril, captopril, carvedilol, cerivastatin, clonidine, clopidrogrel, dalteparin, danaparoid, diliazem, enalapril, fluvastatin, fosinopril, gemfibrozil, hydrochlorothiazide, irbesartan, lepirudin, lisinopril, lovastatin, oprelvekin, pravastatin, prazosin, quinapril, ramipril, saruplase, simvastatin, terazosin, valsartan, or verapamil. The second compound can also be another CRF antagonist.

Similarly, for example, where the compound of the invention is used to treat a sleep disorder, a second compound, e.g., a non-CRF antagonist that is useful for treating sleep disorder, can be administered before, with, or after, administration of the CRF antagonist of the invention. Any such second compound useful for treating sleep disorder may be employed, including but not limited to tachykinin antagonists, melatoninergic agonists, such as melatonin, GABA brain receptor agonists, serotonin receptor (such as 5HT1b, 5HT2c, 5HT7) antagonists, inverse agonists, agonists and other compounds. Specific compounds for treatment of sleep disorder include melatonin, carpipramine, and doxylamine.

Similarly, where a compound of the invention is used to treat depression, a second compound for treating depression can be administered, e.g., one that has a delayed effect, including, without limitation, compounds that are selective serotonin reuptake inhibitors (SSRIs), tricyclic antidepressants, norepinephrine reuptake inhibitors, noradrenaline reuptake inhibitors, lithium, α2-adrenoreceptor agonists, 5HT1A inhibitors, and monoamine oxidase type A inhibitors. Examples of such compounds for treating depression include bupropion, sertraline, fluoxetine, trazodone, citalopram, fluvoxamine, paroxetine, venlafaxine, roboxetine, imipramine, amitriptyline, trimipramine, doxepin, desipramine, nortriptyline, protriptyline, amoxapine, clomipramine, maprotiline, brofaromine, milnacipran, and buspirone.

Similarly, where the compound of the invention is employed to treat migraine or non-migraine headache, it may be co-administered with, for example, non-steroidal anti-inflammatory drugs (NSAIDs), such as aspirin, acetaminophen, ibuprofen, with anti-emetics, with preparations containing ergotamine such as dihydroergotamine, or with agents that modulate serotonin receptors (including those that modulate the 5HT1B, 5HT1D, 5HT1F and 5HT2B receptors) or that mimic the effects of serotonin. Particular agents include sumatriptan, naratriptan, zolmitriptan, rizatriptan, eletriptan, and almotriptan.

Where the compound of the invention is used to treat emesis, it may be combined with other emesis treatments, including, without limitation, tachykinin antagonists, including NK1 antagonists, and 5HT3 antagonists (such as metoclopramide, granisetron, dolasetron, ondansetron and tropisetron).

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform (CDCl$_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

EXAMPLE 1

(E)-1-[2,5,6-Trimethyl-7-(2,4,6-trimethyl-phenyl)-7H-pyrrolo[2,3-d]pyrimidin-4-yl]-propan-1-one oxime and (Z)-1-[2,5,6-Trimethyl-7-(2,4,6-trimethyl-phenyl)-7H-pyrrolo[2,3-d]pyrimidin-4-yl]-propan-1-one oxime A mixture of 1-[2,5,6-trimethyl-7-(2,4,6-trimethyl-phenyl)-7H-pyrrolo[2,3-d]pyrimidin-4-yl]-propan-1-one (598 mg, 1.783 mmol) and hydroxylamine hydrochloride and sodium acetate in methanol was stirred at room temperature overnight The mixture was quenched with water and extracted with ethyl acetate. The organic layer was separated, dried and concentrated to dryness to give 657 mg of a mixture of Z and E isomers of the title compounds. Both isomers were separated by silica gel column chromatography.

(E)-1-[2,5,6-Trimethyl-7-(2,4,6-trimethyl-phenyl)-7H-pyrrolo[2,3-d]pyrimidin-4-yl]-propan-1-one oxime $^1$H NMR(CDCl$_3$) δ9.92(s, 1H), 7.00(s,2H), 3.03(q,2H), 2.70(s, 3H), 2.36(s,3H), 2.26(s,H), 2.00(s,3H), 1.83(s,6H), 1.14(t, 3H)ppm.

(Z)-1-[2,5,6-Trimethyl-7-(2,4,6-trimethyl-phenyl)-7H-pyrrolo[2,3-d]pyrimidin-4-yl]-propan-1-one oxime $^1$H NMR(CDCl$_3$) δ8.55(brs,1H), 7.02(s,2H), 2.73(q,2H), 2.69 (s,3H), 2.37(s,3H), 2.27(s,3H), 2.01(s,3H), 1.84(s,6H), 1.18 (t,3H)pp.

EXAMPLE 2

1-[2-Methyl-8-(2,4,6-trimethyl-phenyl)-quinolin-4-yl]-proyan-1-one (E)-oxime and 1-[2-Methyl-8-(2,4,6-trimethyl-phenyl)-quinolin-4-yl]-propan-1-one (Z)-oxime A mixture of 1-[2-Methyl-8-(2,4,6-trimethyl-phenyl)-quinolin-4-yl]-propan-1-one (200 mg, 0.63 mmol), hydroxylamine hydrochloride (130.95 mg, 1.89 mmol) in ethanol was stirred at room temperature over a weekend. The mixture was concentrated to dryness, then diluted with water, and extracted with chloroform. The organic layer was separated, dried over sodium sulfate and concentrated to dryness to give 240 mg of a 1:1 mixture of the title (E) and (Z)-isomers.

1-[2-Methyl-8-(2,4,6-trimethyl-phenyl)-quinolin-4-yl]-propan-1-one (E)-oxime

1H NMR(CDCl3) δ7.93(d,1H), 7.55(m,1H), 7.46(m,1H), 7.13(s,1H), 6.99(s,2H), 2.88(q,2H), 2.64(s,3H), 2.37(s,3H), 1.88(s,6H), 1.10(t,3H) ppm.

1-[2-Methyl-8-(2,4,6-trimethyl-phenyl)-quinolin-4-yl]-propan-1-one (Z)-oxime

1H NMR(CDCl3) δ7.66(d,1H), 7.53(m,1H), 7.47(m,1H), 7.04(s,1H), 6.98(s,2H), 2.64(s,3H), 2.62(m,2H), 2.37(s,3H), 1.89(s,6H), 1.15(t,3H) ppm.

EXAMPLE 3

(E)1-[2-Methyl-8-(2,4,6-trimethyl-phenyl)-quinolin-4-yl]-propan-1-one-O-methyl-oxime and (Z)-1-[2-Methyl-8-(2,4,6-trimethyl-phenyl)-quinolin-4-yl]-propan-1-one O-methyl-oxime A mixture of 1-[2-methyl-8-(2,4,6-trimethyl-phenyl)-quinolin-4-yl]-propan-1-one (83 mg, 0.26 mmol), methoxylamine hydrochloride (66 mg, 0.78 mmol) and sodium acetate (64 mg, 0.78 mmol) in ethanol (5 ml) was stirred at room temperature overnight. The mixture was treated with 3 ml of MeOH, 2 ml of chloroform, excess of methoxylamine hydrochloride (200 mg) and triethylamine (0.2 ml) and stirred at rt for an additional 15 hr. The mixture was concentrated to dryness, then diluted with water, and extracted with chloroform. The organic layer was separated, dried over sodium sulfate and concentrated to dryness to give 88 mg of a mixture of the title trans and cis-isomers. The isomers was separated by silica gel preparative thin layer chromatography using 7% ethyl acetate in hexane as solvent to give both isomers separated as a white solid.
(E)-1-[2-Methyl-8-(2,4,6-trimethyl-phenyl)-quinolin-4-yl]-propan-1-one O-methyl-oxime 1H NMR(CDCl3) δ7.92(d, 1H), 7.51(m,1H), 7.x(M,1H), 7.13(s,1H), 6.97(s,2H), 4.02 (s,3H), 2.88(q,2H), 2.57(s,3H), 2.36(s,3H), 1.86(s,6H), 1.08 (t,3H) ppm.

(Z)-1-[2-Methyl-8-(2,4,6-trimethyl-phenyl)-quinolin4-yl]-propan-1-one O-methyl-oxime 1H NMR(CDCl3) δ7.60(d,1H), 7.49(m,1H), 7.44(d,1H), 6.97(s,3H), 3.80(s,3H), 2.60(m,2H), 2.60(s,3H), 2.37(s,3H), 1.89(s,6H), 1.13(t,3H)ppm.

EXAMPLE 4

A mixture of (E)- and (Z)-isomers of 1-[3,6-Dimethyl-2-(2,4,6-trimethyl-phenoxy)-pyridin-4-yl]-propan-1-one oxime A mixture of 1-[3,6-dimethyl-2-(2,4,6-trimethyl-phenoxy)-pyridin-4-yl]-propan-1-one (330 mg, 1.11 mmol), hydroxylamine hydrochloride (230.4 mg, 3.33 mmol), and sodium acetate (273 mg, 3.33 mmol) in ethanol (25 ml) was stirred at room temperature over a weekend. The mixture was concentrated to dryness, then diluted with water, and extracted with chloroform. The organic layer was separated, dried over sodium sulfate and concentrated to dryness to give 306 mg of a mixture of the title (E) and (Z)-isomers as a white solid.

1H NMR(CDCl3) δ6.87(s,2H), 6.60(s,0.5H), 6.49(s, 0.5H), 2.65–2.82(m,1H), 2.4–2.6(m,1H), 2.05–2.4(4 sets of s, total of 9H), 1.95–2.05(two sets of S, total of 6H), 1.12(t,1.5H), 1.07(t,1.5H) ppm

EXAMPLE 5

(E)-1-[3,6-Dimethyl-2-(2,4,6-trimethyl-phenoxy)-pyridin-4-yl]-propan-1-one O-methyl-oxime and (Z)-1-[3,6-Dimethyl-2-(2,4,6-trimethyl-phenoxy)-pyridin-4-yl]-propan-1-one O-methyl-oxime A mixture of 1-[3,6-dimethyl-2-(2,4,6-trimethyl-phenoxy)-pyridin-4-yl-propan-1-one (3030 mg, 1.008 mmol), methoxylamine hydrochloride (230.4 mg, 3.33 mmol), and sodium acetate (273 mg, 3.33 mmol) in ethanol (25 ml) was stirred at room temperature over night. The mixture was concentrated to dryness, then diluted with water, and extracted with chloroform. The organic layer was separated, dried (sodium sulfate) and concentrated to dryness to give 231 mg of a mixture of the title (E) and (Z)-isomers as a clear oil. Both isomers were separated by silica gel column chromatography.

(E)-1-[3,6-Dimethyl-2-(2,4,6-trimethyl-phenoxy)-pyridin-4-yl]-propan-1-one O-methyl-oxime 1H NMR (CDCl3) δ6.87(s,2H), 6.58(s,1H), 3.97(s,3H),2.67(q,2H), 2.29(s,6H), 2.22(s,3H), 2.03(s,6H), 1.03(t,3H)ppm.

(Z)-1-[3,6-Dimethyl-2-(2,4,6-trimethyl-phenoxy)-pyridin-4-yl]-propan-1-one O-methyl-oxime 1H NMR(CDCl3) δ6.87(s,2H), 6.43(s,1H), 3.83(s,3H), 2.46(m,2H), 2.29(s,3H), 2.25(s,3H), 2.15(s,3H), 2.05(2 sets of s, 6H), 1.08(t,3H)ppm.

EXAMPLE 6

(E) and (Z)-1-[7-Methyl-1-(2,4,6-trimethyl-phenyl)-1,4-dihydro-2H-pyrimido[4,5-d][1,3]oxazin-5-yl]-propan-1-one oxime A mixture of 1-[7-methyl-1-(2,4,6-trimethyl-phenyl)-1,4-dihydro-2H-pyrimido[4,5-d][1,3]oxazin-5-yl]-propan-1-one (50 mg, 0.154 mmol), hydroxylamine hydrochloride (43 mg, 0.62 mmol), and sodium acetate (57 mg, 0.693 mmol) in ethanol (4 ml) was stirred at room temperature overnight. The mixture was concentrated to dryness, then diluted with water, and extracted with 3 times with ethyl acetate. The organic layer was separated, dried (MgSO4) and concentrated to dryness to give 51 mg of a mixture of the title (E) and (Z)-isomers as a white solid. Both isomers were separated by preparative thin layer chromatography plate with 40% ethyl acetate in hexane as solvent.

1-[7-Methyl-1-(2,4,6-trimethyl-phenyl)-1,4-dihydro-2H-pyrimido[4,5-d][1,3]-oxazin-5-yl]-propan-1-one (E)-oxime, 1H NMR(CDCl3) δ6.94(s,2H), 4.97(s,2H), 4.92(s,2H), 2.93 (m,2H), 2.39(s,3H), 2.30(s,3H), 2.12(s,6H), 1.10(t,3H)ppm.

1-[7-Methyl-1-(2,4,6-trimethyl-phenyl)-1,4dihydro-2H-pyrimido[4,5-d][1,3]oxazin-5-yl]-propan-1-one (Z)-oxime, 1H NMR(CDCl3) δ6.94(s,2H), 4.95(s,2H), 4.78(s,2H), 2.64 (m,2H), 2.40(s,3H), 2.30(s,3H), 2.13(s,6H), 1.09(t,3H)ppm.

EXAMPLE 7

2-(4-Chloro-2,6-dimethyl-phenoxy)-3,6-dimethyl-pyridin-4-yl]-pyridin-2-yl-methanone (E) and (Z)-oxime A mixture of [2-(4-Chloro-2,6-dimethyl-phenoxy)-3,6-dimethyl-pyridin-4-yl]-pyridin-2-yl-methanone (32 mg), hydroxylamine hydrochloride (300 mg), and sodium acetate (40 mg) in methanol (2 ml) was stirred at room temperature over a weekend. The mixture was concentrated to dryness, then diluted with water, brine, and extracted with chloroform. The organic layer was separated, dried (Na$_2$SO$_4$) and concentrated to dryness to give 31 mg of a 4:1 mixture of the title (Z) and (E)-isomer, respectively, as a colorless oil. Both isomers were separated by preparative thin layer chromatography with 2% methanol in chloroform as solvent.

[2-(4-Chloro-2,6-dimethyl-phenoxy)-3,6-dimethyl-pyridin-4-yl]-pyridin-2-yl-methanone (Z)-oxime 1H NMR (CDCl3) δ8.62(s,1H), 7.71(m,1H), 7.60(m,1H), 7.29(m, 1H), 7.05(s,2H), 6.60(s,1H), 2.24(s,3H), 2.15(s,3H), 2.08(s, 6H), ppm.

EXAMPLE 8

1-[2-Methyl-8-(2,4,6-trimethyl-phenyl)-quinolin-4-yl]-propan-1-one O-isobutyl-oxime A mixture of 1-[2-methyl-8-2,4,6-trimethyl-phenyl)quinolin4-yl]-propan-1-one (52 mg), iso-butoxylamine hydrochloride (300 mg), potassium carbonate (50 mg) and sodium acetate (40 mg) in ethanol (2 ml) was stirred at room temperature for 48 hr. The mixture was concentrated to dryness, then diluted with water, brine, and extracted with chloroform. The organic layer was separated, dried (Na$_2$SO$_4$) and concentrated to dryness to give a mixture of the title (Z) and (E)-isomer, respectively. The crude mixture was purified by preparative thin layer chromatography with 7% ethyl acetate in hexane as solvent to give a 6:4 mixture of isomers.

1H NMR(CDCl3) d 7.90(d, 0.4H), 7.62(d, 0.4H), 7.18–7.28(m,2H), 7.24 & 7.13(two sets of s, 1H), 6.98(s, 0.8H), 6.97(s,1.2H), 4.00(m,0.8H), 3.77(m,1.2H), 2.88(m, 0.8H), 2.63(m,1.2H), 2.58&2.57(two sets of s, 3H), 2.37(s, 3H), 2.22&1.85(m,1H), 1.88&1.87(two sets of s, 6H), 1.0–1.2(m,3H), 1.00(d,2H), 0.66(d,1.8H)ppm.

EXAMPLE 9

1-[2,5,6-Trimethyl-7-(2,4,6-trimethyl-phenyl)-7H-pyrrolo[2,3-d]pyrimidin-4-yl]-ethanone (E) and (Z)-O-methyl-oxime A mixture of 1-[2,5,6-trimethyl-7-(2,4,6-trimethyl-phenyl)-7H-pyrrolo[2,3-d]pyrimidin-4-yl]-ethanone (100 mg, 0.311 mmol), methoxylamine hydrochloride (129.8 mg, 1.56mmol), and sodium acetate (127.63 mg, 1.56 mmol) in ethanol (10 ml) was stirred at room temperature overnight. The mixture was concentrated to dryness, then diluted with water, and extracted with chloroform. The organic layer was separated, dried (sodium sulfate) and concentrated to dryness to give 107 mg of a mixture of the title (E) and (Z)-isomers as a yellow solid. Both isomers were separated by silica gel column chromatography.

(Z)-1-[2,5,6-Trimethyl-7-(2,4,6-trimethyl-phenyl)-7H-pyrrolo[2,3-d]pyrimidin-4-yl]-ethanone (Z)-O-methyl-oxime 1H NMR(CDCl3) d 7.01(s,2H), 3.86(s,1H), 2.68(s,3H), 2.35(s,3H), 2.33(s,3H), 2.21(s,3H), 2.00(s,3H), 1.85(s,3H), 1.79(s,3H) ppm.

(E)-1-[2,5,6-Trimethyl-7-(2,4,6-trimethyl-phenyl)-7H-pyrrolo[2,3-d]pyrimidin-4-yl]-ethanone (Z)-O-methyl-oxime 1H NMR(CDCl3) d 7.02(s,2H), 4.06(s,3H), 2.68(d,3H), 2.35(s,3H), 2.29(s,3H), 2.01(s,3H), 1.81(s,6H) ppm.

EXAMPLE 10

Propyl-carbamic acid 1-[2-(4-chloro-2,6-dimethyl-phenoxy)-3,6-dimethyl-pyridin-4-yl]-2,2,2-trifluoro-ethyl ester A mixture of 1-[2-(4-chloro-2,6-dimethyl-phenoxy)-3,6-dimethyl-pyridin-4-yl]-2,2,2-trifluoro-ethanol (21 mg, 0.0589 mmol), propyl isocyanate (0.1 ml), dimethylaminopyridine (20 mg) in dichloromethane (2 ml) was heated at reflux for 6 hrs. The mixture was quenched with water and extracted with chloroform. The organic layer was separated, dried and concentrated to give 23 mg of yellow solid. The solid was purified by preparative thin layer chromatography (run in 20% ethyl acetate in hexane) to give the title compound as a white solid.

1H NMR(CDCl3) 7.03(s,2H), 6.62(s,1H), 5.11(m,1H), 3.24(m,2H),2.19(s,3H), 2.17(s,3H), 2.03(s,6H), 1.5–1.7(m, 2H), 0.98(t,3H)ppm.

EXAMPLE 11

Methyl-carbamic acid 1-[3,6-dimethyl-2(2,4,6-trimethyl-phenoxy)-pyridin-4-yl]-2,2,2-trifluoro-ethyl ester A mixture of 1-[2-(2,4,6-trimethyl-phenoxy)-3,6-dimethyl-pyridin-4-yl]3-2,2,2-trifluoro-ethanol (100 mg, 0.295 mmol), methyl isocyanate (0.25 ml), dimethylaminopyridine (20 mg) in dichloromethane (2 ml) was heated at reflux for 6 hrs. The mixture was quenched with water and extracted with chloroform. The organic layer was separated, dried and concentrated to give 120 mg of yellow solid. The solid was purified by silica gel column chromatography using chloroform as eluent to give 77 mg of the title compound as a white solid.

1H NMR(CDCl3) 6.86(s,2H), 6.81(s,1H), 6.39(m,1H), 4.93(m,1H), 2.84(d,3H), 2.41(s,3H), 2.28(s,3H), 2.24(s,3H), 2.02(s,6H) ppm.

EXAMPLE 12

Methyl-carbamic acid 1-[3,6-dimethyl-2-(2,4,6-trimethyl-phenoxy)-pyridin-]4-yl-propyl ester A mixture of 1-[3,6dimethyl-2-(2,4,6-trimethyl-phenoxy)-pyridin-4-yl]-propan-1-ol (100 mg, 0.334 mmol), methyl isocyanate (0.5 ml), dimethylaminopyridine (20 mg) in dichloromethane (3 ml) was heated at reflux for 6 hrs. The mixture was quenched with water and extracted with chloroform. The organic layer was separated, dried and concentrated to give the crude material which was purified by preparative thin layer chromatography using 20% ethyl acetate in hexane as solvent to give the title compound as a white solid, mp. 148–150.5° C.

$^1$H NMR(CDCl3) 6.85(s,2H), 6.67(s,1H), 5.80(m,1H), 4.71(m,1H), 2.78(d,3H), 2.34(s,3H), 2.27(s,3H), 2.20(s,3H), 2.02(s,6H), 1.7–1.85(m,2H), 0.94(t,3H),

EXAMPLE 13

Methyl-carbamic acid 2,2,2-trifluoro-1-[2-methyl-8-(2,4,6-trimethyl-phenyl)quinolin-4-yl]-ethyl ester A mixture of 2,2,2-trifluoro-1-[2-methyl-8-(2,4,6-trimethyl-phenyl)quinolin-4-yl]-ethanol (50 mg), methyl isocyanate (0.5 ml), triethylamine (0.1 ml) in dichloromethane (2 ml) was heated at reflux for 2 hrs. The mixture was quenched with water and extracted with chloroform. The organic layer was separated, dried and concentrated to give the crude material which was purified by silica gel column chromatography using chloroform as eluent to give the title compound as a white solid.

$^1$H NMR(CDCl3) 6.85(s,2H), 6.67(s,1H), 5.80(m, 1H), 4.71 (m, 1H), 2.78(d,3H), 2.34(s,3H), 2.27(s,3H), 2.20(s, 3H), 2.02(s,6H), 1.7–1.85(m,2H), 0.94(t,3H), ppm

EXAMPLE 14

Methyl-carbamic acid 1-methyl-2-[2,5,6-trimethyl-7-(2,4,6-trimethyl-phenyl)-7H-pyrrolo[2,3d]pyrimidin-4-ylamino]butyl ester A mixture of 3-[2,5,6trimethyl-7-(2,4,6-trimethyl-phenyl)-7H-pyrrolo[2,3-d]pyrimidin-4-ylamino]-pentan-2-ol (200 mg, 0.526 mmol), methyl isocyanate (0.87 ml), dimethylaminopyridine (19 mg, 0.158 mmol) in dichloromethane (5 ml) was heated at reflux for 1 hr. The mixture was quenched with water and extracted with chloroform. The organic layer was separated, dried and concentrated to give the crude material (230 mg) which was purified by silica gel flash column chromatography using 3% methanol in chloroform as eluent to give the title compound (190 mg) as a white foam.

$^1$H NMR(CDCl3) d 6.5(s,2H), 4.9–5.2(m,2H), 4.4–4.7(m, 2H), 2.72–2.77(m,3H), 2.39(s,6H), 2.32(s,3H), 1.88(s,3H), 1.83(s,6H), 1.4–1.8(m,2H), 1.3(m,3H) ppm.

EXAMPLE 15

Methyl-carbamic acid 1-[2,5,6-trimethyl-7-(2,4,6-trimethyl-phenyl)-7H-pyrrolo[2,3-d]pyrimidin-4-yl]-propyl ester A mixture of 1-[2,5,6-trimethyl-7-(2,4,6-trimethyl-phenyl)-7H-pyrrolo[2,3-d]pyrimidin-4-yl]-propan-1-ol(62 mg, 0.184 mmol), methyl isocyanate (0.25 ml), dimethylaminopyridine (20 mg) in dichloromethane (2 ml) was heated at reflux for 1 hr. Additional methyl isocyanate (0.25 ml) was added and the resulting mixture was stirred at room temperature overnight. The mixture was quenched with water and extracted with chloroform. The organic layer was separated, dried and concentrated to give a yellow foam (95 mg). The foam was purified by preparative thin layer chromatography plate in 10% methanol in chloroform, then in 20% methanol in chloroform as solvent to give the title compound (29 mg) as an off-white solid.

¹H NMR(CDCl3) d 6.99(s,2H), 6.24(m,1H), 5.12(m,1H), 2.77(d,3H), 2.66(s,3H), 2.49(s,3H), 2.34(s,3H), 2.069m, 2H), 1.98(s,3H), 1.79(d,6H), 1.00(t,3H) ppm.

EXAMPLE 16

Methyl-carbamic acid 1-[7-methyl-1-(2,4,6-trimethyl-phenyl)-1,4-dihydro-2H-pyrimido[4,5-d][1,3]-oxazin-5-yl]-propyl ester A mixture of 1-[7-methyl-1-(2,4,6-trimethyl-phenyl)-1,4-dihydro-2H-pyrimido[4,5-d][1,3]oxazin-5-yl]-propan-1-ol (50 mg), methyl isocyanate (0.25 ml), dimethylaminopyridine (37 mg) in dichloromethane (2 ml) was heated at reflux for 1 hr. The mixture was quenched with water and extracted with chloroform. The organic layer was separated, dried and concentrated to give a clear oil (70 mg). The oil was purified by silica gel thin layer chromatography plate using 40% ethyl acetate in hexane as solvent to give 36 mg of the title compound.

¹H NMR(CDCl3) d 8.11(d,1H), 6.92(s,2H), 4.8–5.6(m, 6H), 2.78(d,3H), 2.34(s,3H), 2.29(s,3H), 2.12(s,3H), 2.10(s, 3H), 1.8–2.1 (m,2H), 0.95(m,3H) ppm.

EXAMPLE 17

1-{1-[3,6-Dimethyl-2-(2,4,6-trimethyl-phenoxy)-pyridin-4-yl]-propyl}-3-methyl-urea A mixture of 1-[3,6-dimethyl-2-(2,4,6-trimethyl-phenoxy)-pyridin-4-yl]-propylamine (26.5 mg), methyl isocyanate (0.05 ml), in dichloroethane (1 ml) was heated at reflux overnight. The mixture was quenched with water and extracted with chloroform. The organic layer was separated, dried and concentrated to give 27.1 mg of white solid. The solid was purified by preparative thin layer chromatography using 5% methanol in chloroform as solvent to give the title compound as a white solid.

¹H NMR(CDCl3) d 6.86(s,2H), 6.67(s,1H), 4.89(m,2H), 4.459m,1H), 2.71–2.83(m,3H), 2.37(s,3H), 2.28(s,3H), 2.16 (s,3H), 2.02(s,6H), 1.6–1.8(m,2H), 0.95(m,3H) ppm.

EXAMPLE 18

Methyl-carbamic acid 2,2,2-trifluoro-1-[7-methyl-1-(2,4, 6-trimethyl-phenyl)-1,4-dihydro-2H-pyrimido[4,5-d][1,3] oxazin-5-yl]-ethyl ester A mixture of 2,2,2-trifluoro-1-[7-methyl-1-(2,4,6-trimethyl-phenyl)-1,4-dihydro-2H-pyrimido[4,5-d][1,3] oxazin-5yl]-ethanol (26 mg), methyl isocyanate (0.12 ml), dimethylaminopyridine (27 mg) in dichloromethane (2 ml) was heated at reflux for 2 hrs. The mixture was quenched with water and extracted with chloroform. The organic layer was separated, dried and concentrated to give the crude material which was purified by silica gel column chromatography using chloroform as eluent to give 21 mg of the title compound as a white solid.

¹H NMR(CDCl3) d 6.93(m,2H), 5.99(q,1H), 5.22(m,1H), 4.8–5.2(m,4H), 2.86(d,3H), 2.34(s,3H), 2.30(s,3H), 2.12(s, 3H), 2.10(s,3H) ppm.

EXAMPLE 19

1-Methyl-3-{1-[2-methyl-8-(2,4,6-trimethyl-phenyl)-quinolin-4-yl]-propyl}urea

A mixture of 1-[2-methyl-8-(2,4,6-trimethyl-phenyl)-quinolin-4-yl]-propylamine (55 mg), methyl isocyanate (0.3 ml), in dichloroethane (1 ml) was heated at 60° C. for 1 hrs. The mixture was quenched with water and extracted with chloroform. The organic layer was separated, dried and concentrated to give the crude material as a colorless oil. The oil was purified by preparative thin layer chromatography using 3% methanol in chloroform as solvent to give 42 mg of the title compound as a white glass foam.

1 H NMR(CDCl3) d 8.11(s, 1H), 7.56(m, 1H), 7.45(m, 1H), 7.12(s,1H), 6.97(d,2H), 5.46(m,1H), 5.12(brs,1H), 4.50 (brs,1H), 2.69(d,3H), 2.36(s,3H), 1.7–2.0(m,2H), 1.92(s, 3H), 1.81(s,3H), 0.99(t,3H) ppm.

EXAMPLE 20

N-{Thiazol-2-yl-[2,5,6-trimethyl-7-(2,4,6-trimethyl-phenyl)-7H-pyrrolo[2,3-d]pyrimidin-4-yl]-methyl}) acetamide A mixture of thiazol-2-yl-[2,5,6-trimethyl-7-(2,4,6-trimethyl-phenyl)-7H-pyrrolo[2,3-d]pyrimidin-4-yl]-methylamine (50 mg, 0.126 mmol) and acetic anhydride (0.1 ml) in dry THF (2 ml) was stirred at room temperature for ½ hr. The mixture was quenched with water and extracted with ethyl acetate. The organic layer was separated, dried and concentrated to give the title compound.

1H NMR(CDCl3) d 7.95(brs,1H), 7.68(d,1H), 7.25(d, 1H), 7.09(d,1H), 6.99(s,2H), 2.62(s,3H), 2.53(s,3H), 2.34(s, 3H), 2.15(s,3H), 1.98(s,3H), 1.83(s,3H) ppm.

EXAMPLE 21

1-Methyl-3-{thiazol-2-yl-[2,5,6-trimethyl-7-(2,4,6-trimethyl-phenyl)-7H-pyrrolo[2.3-d]pyrimidin-4-yl]-methyl}-urea A mixture of thiazol-2-yl-2(2,4,6-trimethyl-phenyl)-7H-pyrrolo[2,3-d]pyrimidin-4-yl]-methylamine (55 mg, 0.14 mmol) and methyl isocyanate (0.3 ml) in dichloroethane (2 ml) was heated at reflux for 1 hr. The mixture was quenched with water and extracted with ethyl acetate. The organic layer was separated, dried and concentrated to give the crude material which was purified by thin layer chromatography plate using 5% methanol in chloroform as solvent to give 28 mg of the title compound as a colorless foam.

1H NMR(CDCl3) d 7.67(d,1H), 7.24(d,1H), 7.07(d,1H), 6.98(s,2H), 4.99(s,1H), 2.75(d,3H), 2.53(s,3H), 2.40(s,3H), 2.34(s,3H), 1.98(s,3H), 1.82(s,3H) ppm.

What is claimed is:
1. A compound having Formula VII:

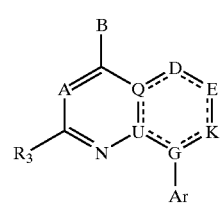

wherein:
the dashed line in the figure represents alternating single and double bonds;
A is CR$^7$;
B is —C(R$^2$)(=NY$^1$R$^1$), —(Y$^3$)—C(R$^2$)(=NY$^1$R$^1$), —NR$^{16}$R$^2$, —NHCR$^{16}$R$^2$, —SCHR$^{16}$R$^2$, —CHR$^{16}$R$^2$, —C(OH)R$^{16}$R$^2$, —CHR$^{16}$(OR$^{12}$), —C(F)R$^{16}$R$^2$, —C(OMe)R$^{16}$R$^2$, —CR$^{16}$(=CR$^2$R$^1$), —C(N(C$_1$–C$_4$ alkyl)R$^2$)(=NY$^1$R$^1$), —Y$^3$C(Y$^2$R$^2$)(=NY$^1$R$^1$), or —V$^1$—V$^2$;

Q and U are carbon;

$V^1$ is ($C_0$–$C_1$ alkylene), O, S, NH, or —N($C_1$–$C_4$ alkylene);

$V^2$ is a five to eight membered carbocyclic ring wherein one or two of the carbocyclic ring carbons may optionally and independently be replaced by O, S, N, or $NZ^3$, and the ring optionally consists of one to three double bonds, further wherein the ring is optionally substituted with from one to two $R^{22}$ substituents and wherein the ring or $R^{22}$ consists of the moiety C=N—$Y^1$—($C_1$–$C_4$ alkylene);

$X^2$ is S or O;

$Y^1$, $Y^2$, and $Y^3$ are each independently O, S, NH, or —N($C_1$–$C_4$ alkyl);

wherein:
D and E are independently selected from $CR^4$;
K is $CR^6$;
G is carbon;
and wherein the ring consisting of D, E, K, G, in Formula VII is an aromatic carbocyclic ring having alternating single and double bonds;
$Z^2$ is hydrogen or $C_1$–$C_4$ alkyl;
$Z^3$ is hydrogen, $C_1$–$C_4$ alkyl, or benzyl;
$Z^4$ is N, CH, or C($C_1$–$C_2$ alkyl) when single bonded to both adjacent ring atoms, and $Z^4$ is carbon when double bonded to either adjacent ring atom;
Ar is $C_6$–$C_{10}$ aryl or 5–10 membered heteroaryl, wherein Ar is optionally substituted with from one to four $R^{13}$ substituents, and wherein two adjacent $R^{13}$ substituents optionally form a five to seven membered ring structure fused to Ar, which five to seven membered ring may be further substituted with from one to four independently selected $R^{13}$ substituents, and which five to seven membered ring optionally consists of one to three double bonds and one to three heteroatoms selected from O, S, N, and $NZ^3$;
$R^1$ is H, $C_1$–$C_6$ alkyl, $C_6$–$C_{10}$ aryl, 5–10 membered heteroaryl, ($C_1$–$C_6$ alkylene)-($C_6$–$C_{10}$ aryl), ($C_1$–$C_6$ alkylene)-(5–10 membered heteroaryl), $C_3$–$C_8$ cycloalkyl, ($C_1$–$C_6$ alkylene)-($C_3$–$C_8$ cycloalkyl), $C_3$–$C_8$ spiroalkyl, $C_3$–$C_8$ heteroarylalkyl, or ($C_1$–$C_4$ alkylene)-($C_3$–$C_8$ heteroarylalkyl), wherein each of said $R^1$ groups is optionally substituted with one or two substituents independently selected from hydroxy, fluoro, chloro, bromo, iodo, $C_1$–$C_6$ alkyl, alkoxy, $CF_3$, —C(=O)O—($C_1$–$C_4$ alkyl), —OC(=O)($C_1$–$C_4$ alkyl), $C_1$–$C_6$ alkyl, $C_3$–$C_8$ cycloalkyl, —OC(=O)N($C_1$–$C_4$ alkyl)($C_1$–$C_2$ alkyl), —NHCO($C_1$–$C_4$ alkyl), —COOH, —COO($C_1$–$C_4$ alkyl), —CONH$_2$, —CONH($C_1$–$C_4$ alkyl), —CON($C_1$–$C_4$ alkyl)($C_1$–$C_2$ alkyl), —S($C_1$–$C_4$ alkyl), CN, —NO$_2$, —SO($C_1$–$C_4$ alkyl), —SO$_2$($C_1$–$C_4$ alkyl), —SO$_2$NH($C_1$–$C_4$ alkyl) —SO$_2$N($C_1$–$C_4$ alkyl)($C_1$–$C_2$ alkyl), and $NR^{17}R^{18}$, wherein each of the alkyl moieties of said $R^1$ groups that consist of three or more carbons optionally consists of one or two double or triple bonds and wherein each of the $C_1$–$C_2$ alkyl moieties in said RI groups optionally consists of one double or triple bond, provided that when $Y^1$ is S, or O, and $Y^1$ is attached to $R^1$, then $R^1$ is not H;

$R^2$ is H, $C_1$–$C_6$ alkyl, $C_6$–$C_{10}$ aryl, 5–10 membered heteroaryl, ($C_1$–$C_6$ alkylene)-$Y^1$—($C_1$–$C_6$ alkyl), ($C_1$–$C_6$ alkylene)-($C_6$–$C_{10}$ aryl), ($C_1$–$C_6$ alkylene)-(5–10 membered heteroaryl), $C_3$–$C_8$ cycloalkyl, ($C_1$–$C_6$ alkylene)-($C_3$–$C_8$ cycloalkyl), wherein each of said $R^2$ groups is optionally substituted with from one to three substituents independently selected from chloro, fluoro and $C_1$–$C_4$ alkyl, or with one substituent selected from hydroxy, bromo, iodo, $C_1$–$C_6$ alkoxy, —OC(=O)($C_1$–$C_6$ alkyl), —OC(=O)NH($C_1C_4$ alkyl), —OC(=O)N($C_1$–$C_4$ alkyl)($C_1$–$C_2$ alkyl), —S($C_1$–$C_6$ alkyl), amino, —NH($C_1$–$C_2$ alkyl), —N($C_1$–$C_2$ alkyl)($C_1$–$C_4$ alkyl), —N($C_1$–$C_4$ alkyl)-CO—($C_1$–$C_4$ alkyl), —NHCO($C_1$–$C_4$ alkyl), —COOH, —COO($C_1$–$C_4$ alkyl), —CONH($C_1$–$C_4$ alkyl), —CON($C_1$–$C_4$ alkyl)($C_1$–$C_2$ alkyl), —SH, —CN, —NO$_2$, —SO($C_1$–$C_4$ alkyl), —SO$_2$($C_1$–$C_4$ alkyl), —SO$_2$NH($C_1$–$C_4$ alkyl) and —SO$_2$N($C_1$–$C_4$ alkyl)($C_1$–$C_2$ alkyl), provided that when $Y^2$ is S, or O, then $R^2$ is not H;

$R^3$ is hydrogen, $C_1$–$C_4$ alkyl, —O($C_1$–$C_4$ alkyl), chloro, fluoro, bromo, iodo, $CF_3$, ($C_1$–$C_2$ alkylene)O($C_1$–$C_2$ alkyl), ($C_1$–$C_2$ alkylene)-OH, —S($C_1$–$C_4$ alkyl) or —SO$_2$($C_1$–$C_4$ alkyl);

$R^4$ and $R^6$ are each independently hydrogen, OH, ($C_1$–$C_6$ alkyl), or one of $R^4$ or $R^6$ is hydrogen, ($C_1$–$C_4$ alkyl), $CF_3$, $CH_2CF_3$, $CF_2CF_3$, and the other is —CO($C_1$–$C_4$ alkyl), —S($C_1$–$C_2$ alkyl), —O($C_1$–$C_4$ alkyl), or —NH($C_1$–$C_4$ alkyl), wherein adjacent substituents at D and E may optionally form a 5 to 6 membered carbocyclic or heterocyclic ring fused to the bicyclic ring consisting of D and E, wherein said heterocyclic ring consists of 1 to 3 heteroatoms, and wherein $CR^4R^6$ optionally forms a $C_3$–$C_5$ carbocyclic ring wherein one member of said $C_3$–$C_5$ carbocyclic ring may optionally be replaced with O;

$R^5$ is hydrogen, $C_1$–$C_6$ alkyl, fluoro, chloro, bromo, iodo, hydroxy, cyano, amino, ($C_1$–$C_2$ alkylene)-OH, ($C_1$–$C_2$ alkylene)-O($C_1$–$C_4$ alkyl), —CH$_2$OCF$_3$, $CF_3$, —CH$_2$SMe, —S($C_1$–$C_3$ alkyl), nitro, —O($C_1$–$C_4$ alkyl), —N($C_1$–$C_4$ alkyl)($C_1$–$C_2$ alkyl), —S($C_1$–$C_4$ alkyl), —C(=O)($C_1$–$C_4$ alkyl), —C(=NOH)($C_1$–$C_4$ alkyl), —C(=NO—($C_1$–$C_4$ alkyl))($C_1$–$C_4$ alkyl), —C(=O)H, —C(=O)O($C_1$–$C_4$alkyl), —CONR$^{17}$R$^{18}$, wherein each of the $C_1$–$C_4$ alkyl moieties of $R^5$ optionally consists of one double or triple bond and is optionally substituted with one substituent selected from hydroxy, amino, NHCOCH$_3$, NH($C_1$–$C_2$ alkyl), and N($C_1$–$C_2$ alkyl)$_2$;

$R^7$ is hydrogen, $C_1$–$C_4$ alkyl, chloro, fluoro, iodo, bromo, hydroxy, —O($C_1$–$C_4$ alkyl), —C(=O)($C_1$–$C_4$ alkyl), —C(=O)O($C_1$–$C_4$ alkyl), —OCF$_3$, —CF$_3$, —CH$_2$OH or —CH$_2$O($C_1$–$C_2$ alkyl;

$R^8$, $R^9$, and $R^{10}$ are independently hydrogen or $C_1$–$C_4$ alkyl;

$R^{11}$ and $R^{12}$ are independently hydrogen, trifluoromethyl or methyl, or one of $R^{11}$ and $R^{12}$ is cyano and the other is hydrogen or methyl;

$R^{13}$ is fluoro, chloro, iodo, bromo, $C_1$–$C_6$ alkyl, $C_3$–$C_8$ cycloalkyl, ($C_1$–$C_4$ alkylene)-($C_3$–$C_8$ cycloalkyl), —O($C_1$–$C_6$ alkyl), —O($C_3$–$C_8$ cycloalkyl), —O—($C_1$–$C_4$ alkylene)-($C_3$–$C_8$ cycloalkyl), formyl, OH, OCF$_3$, OCHF$_2$, ($C_1$–$C_4$ alkylene)-OH, ($C_1$–$C_4$ alkylene)-O—($C_1$–$C_2$ alkyl), —CN, —CF$_3$, CHF$_2$, NO$_2$, —NH$_2$, —NH($C_1$–$C_4$ alkyl), —N($C_1$–$C_2$ alkyl)($C_1$–$C_6$ alkyl), —OC(=O)($C_1$–$C_4$ alkyl), ($C_1$–$C_4$ alkylene)-O—($C_1$–$C_4$ alkyl), —S($C_1$–$C_6$ alkyl), ($C_1$–$C_4$ alkylene)-S—($C_1$–$C_4$ alkyl), —C(=O)O($C_1$–$C_4$ alkyl), —C(=O)($C_1$–$C_4$ alkyl), ($C_0$–$C_2$ alkylene)-C(=N—O($C_0$–$C_4$ alkyl)), —COOH, —SO$_2$NH($C_1$–$C_4$ alkyl), —SO$_2$N($C_1$–$C_2$ alkyl)($C_1$–$C_4$ alkyl), —SO$_2$NH$_2$, —NHSO$_2$($C_1$–$C_4$ alkyl), —S($C_1$–$C_6$ alkyl), —$SO_2$($C_1$–$C_6$ alkyl), —$CONR^{17}R^{18}$, ($C_1$–$C_2$ alkylene)$NR^{17}R^1$ and $C_3$–$C_8$ carbocyclic ring in which one or two carbon atoms may be replaced with O, S, or N to form a heterocyclic ring and wherein said carbocyclic or heterocyclic ring may optionally consist of one to three double bonds, and wherein each of the $C_1$–$C_4$ alkyl and $C_1$–$C_6$ alkyl moieties in said $R^{13}$ group optionally has one or two double bonds, and said $C_1$–$C_4$ alkylene and said $C_1$–$C_6$ alkyl in said $R^{13}$ group is optionally substituted with $C_1$–$C_4$ alkyl or F;

$R^{14}$ and $R^{15}$ are independently selected from H, $C_1$–$C_4$ alkyl, —$CH_2$($C_3$–$C_8$ cycloalkyl), and $C_3$–$C_8$ cycloalkyl;

$R^{16}$ is —$R^{19}$—C(=N—$Y^1R^1$)—$R^{20}$, wherein each alkyl or alkylene group in said $R^{16}$ group optionally consists of one or two double or triple bonds;

$R^{17}$ and $R^{18}$ are independently H, $C_1$–$C_6$ alkyl, or $C_3$–$C_8$ heterocycloalkyl; or $NR^{17}R^{18}$ forms a $C_4$–$C_6$ heterocyclo ring which is optionally substituted with hydrogen, $C_1$–$C_6$ alkyl, $CONH_2$, CO[N($C_0$–$C_4$ alkyl)($C_0$–$C_4$ alkyl)], or $C_4$–$C_8$ heterocycloalkyl;

$R^{19}$ is $C_1$–$C_6$ alkylene, ($C_1$–$C_6$ alkylene)-$Y^1$-(alkylene), CO, CS, SO, $SO_2$, wherein said alkylene is optionally substituted with hydroxy, fluoro, chloro, bromo, iodo, $C_1$–$C_4$ alkoxy, $CF_3$, $CHF_2$, O—$CF_3$, $OCHF_2$, —C(=O)O—($C_{C4}$ alkyl), —OC(=O) ($C_1$–$C_4$ alkyl), —OC(=O)N($C_1$–$C_4$ alkyl)($C_1$–$C_2$ alkyl), —NHCO($C_1$–$C_4$ alkyl), —COOH, —COO ($C_1$–$C_4$ alkyl), —CONH($C_1$–$C_4$ alkyl), —CON ($C_1$–$C_4$ alkyl)($C_1$–$C_2$ alkyl), —S($C_1$–$C_4$ alkyl), CN, —$NO_2$, —SO($C_1$–$C_4$ alkyl), —$SO_2$($C_1$–$C_4$ alkyl), —$SO_2$NH($C_1$–$C_4$ alkyl) or —$SO_2$N($C_1$–$C_4$ alkyl) ($C_1$–$C_2$ alkyl);

$R^{20}$ is hydrogen, $C_1$–$C_4$ alkyl, ($C_0$–$C_4$ alkylene)-$NR^{17}R^{18}$, or ($C_1$–$C_6$ alkylene)-G'-$R^{21}$, wherein G' is oxygen or sulfur;

$R^{21}$ is hydrogen, $CF_3$, or $C_1$–$C_4$ alkyl; and $R^{22}$ is hydrogen, $C_1$–$C_4$ alkyl, —O($C_1$–$C_4$ alkyl), chloro, fluoro, bromo, iodo, $CF_3$, ($C_1$–$C_2$ alkylene) O($C_1$–$C_2$ alkyl), ($C_1$–$C_2$ alkylene)-OH, —S($C_1$–$C_4$ alkyl), —$SO_2$($C_1$–$C_4$ alkyl); or C=N—$Y^1$—($C_1$–$C_4$ alkyl);

and wherein, unless otherwise indicated, heteroaryl consists of one to five heteroatoms selected from S, SO, $SO_2$, N, and $NZ^3$ and consists of no S—S, —O—, or S—O bonds, and heterocyclyl consists of one to four heteroatoms selected from O, S, N, or $NZ^3$, and one to three double bonds, and alkyl, alkoxy, spiroalkyl, cycloalkyl, and heterocycloalkyl optionally consist of from one to three double or triple bonds;

or a pharmaceutically acceptable salt or prodrug of the compound.

2. A compound of claim 1 having Formula VII, wherein A, D, E, K, G, U and Q are carbon moieties and the ring defined by D, E, K, G, U and Q is an aromatic ring, having alternating single and double bonds and wherein B is —C($R^2$)(=N—$OR^1$), —C($R^2$)(=N—NH—$R^1$), or —C($R^2$)(=N—N(($C_1$–$C_4$) alkyl)$R^1$).

3. A compound of claim 1 of the Formula VII wherein said ring consisting of D, E, K, G is a benzo ring, A is CH or CMe, B is —C($R^2$)(=N—O—$R^1$), and $R^2$ is aryl, $C_1$–$C_4$ alkyl, $C_3$–$C_8$ cycloalkyl, $C_3$–$C_8$ heterocycloalkyl, ($C_1$–$C_4$ alkylene)-($C_3$–$C_8$ heterocycloalkyl), ($C_1$–$C_4$ alkylene)-O—($C_1$–$C_4$ alkyl), $CF_3$, or $CF_2CF_3$.

4. A compound of claim 3 wherein $R_2$ is $C_1$–$C_4$ alkyl, $CF_3$, or $CF_2CF_3$, $R^1$ is H, $C_1$–$C_4$ alkyl, $C_3$–$C_8$ cycloalkyl, ($C_1$–$C_4$ alkylene)-O—($C_1$–$C_4$ alkyl), or —$C_1$–$C_4$ alkyl-OH and Ar is phenyl, thiazolyl, naphthyl, thienyl, benzothienyl, pyridyl, quinolyl, quinazolinyl, quinoxalinyl, pyrazinyl, pyrimidinyl, imidazolyl, furanyl, benzimidazolyl, benzofuranyl, benzothiazolyl, benzisoxazolyl, isothiazolyl, pyrazolyl, pyrrolyl, indolyl, pyrrolopyridyl, oxazolyl and benzoxazolyl, or benzothiadiazole.

5. A compound of claim 4 wherein Ar is phenyl having two or three $R^{13}$ substituents independently selected from $C_1$–$C_4$ alkyl, $C_3$–$C_8$ cycloalkyl, ($C_1$–$C_2$ alkylene)-($C_3$–$C_8$ cycloalkyl), —O—($C_1$–$C_2$ alkylene)($C_3$–$C_8$ cycloalkyl), —O—($C_3$–$C_8$ cycloalkyl), —O—($C_1$–$C_4$ alkyl), ($C_1$–$C_4$ alkylene)-O—($C_1$–$C_4$ alkyl), $CF_3$, —$OCF_3$, —CHO, ($C_1$–$C_4$ alkylene)-OH, —C(OH)($C_1$–$C_4$ alkyl)($C_1$–$C_4$ alkyl), cyano, chloro, fluoro, bromo and iodo, wherein each of the foregoing ($C_1$–$C_4$) alkyl groups optionally contains one double or triple bond, $R^1$ is H, $C_1$–$C_4$ alkyl, ($C_1$–$C_4$ alkylene)-OH, ($C_1$–$C_4$ alkylene)-O—($C_1$–$C_4$ alkyl), $R^2$ is methyl, ethyl, pyridin-2-yl, or trifluoromethyl, $R^3$ is methyl, each of $R^4$ and $R^6$ is, independently, hydrogen or methyl, and $R^{13}$ is methyl.

6. A compound of claim 1 of Formula VII wherein said ring consisting of D, E, K, and G is benzo, A is CH or CMe, B is $NR^{16}R^2$, $Y^1$ is O, $R^1$ is H, $C_1$–$C_4$ alkyl, $C_3$–$C_8$ cycloalkyl, ($C_1$–$C_4$ alkylene)-O—($C_1$–$C_4$ alkyl), or —$C_1$–$C_4$ alkyl-OH, $R^2$ is aryl, $C_1$–$C_4$ alkyl, $C_3$–$C_8$ cycloalkyl, —$C_1$–$C_4$ alkyl-O—$C_1$–$C_4$ alkyl, $CF_3$, or $CF_2CF_3$, $R^3$ is $C_1$–$C_4$ alkyl, chloro, fluoro, bromo, iodo or —O—($C_1$–$C_4$) alkyl, each of $R^4$ and $R^6$ is, independently, hydrogen or $C_1$–$C_4$ alkyl, and Ar is phenyl having two or three $R^{13}$ substituents independently selected from $C_1$–$C_4$ alkyl, —O—(C–$C_4$ alkyl), ($C_1$–$C_4$ alkylene)-O—($C_1$–$C_4$ alkyl), $CF_3$, —$OCF_3$, —CHO, ($C_1$–$C_4$ alkylene)-OH, —C(OH)($C_1$–$C_4$ alkyl)($C_1$–$C_4$ alkyl), cyano, chloro, fluoro, bromo and iodo, wherein each of the foregoing ($C_1$–$C_4$) alkyl groups optionally consists of one double or triple bond.

7. A compound of claim 6 wherein $R^1$ is H or $C_1$–$C_4$ alkyl, $R^2$ is methyl, ethyl, pyridin-2-yl, or trifluoromethyl, $R^3$ is methyl, each of $R^4$ and $R^6$ is, independently, hydrogen or methyl, $R^{13}$ is methyl, $R^{14}$ and $R^{15}$ are independently H or $C_1$–$C_4$ alkyl, and $R^{16}$ does not contain said optional double or triple bond.

8. A compound of claim 1 selected from the group consisting of:

1-[2-Methyl-8-(2,4,6-trimethyl-phenyl)-quinolin-4-yl]-propan-1-one (E)-oxime;

1-[2-Methyl-8-(2,4,6-trimethyl-phenyl)-quinolin-4-yl]-propan-1-one (Z)-oxime;

1-[2-Methyl-8-(2,4,6-trimethyl-phenyl)-quinolin-4-yl]-propan-1-one (E)-O-methyl-oxime;

1-[2-Methyl-8-(2,4,6-trimethyl-phenyl)-quinolin-4-yl]-propan-1-one O-methyl-oxime;

1-[2-Methyl-8-(2,4,6-trimethyl-phenyl)-quinolin-4-yl]-propan-1-one O-isobutyl-oxime;

1-[2-Methyl-8-(2,4,6-trimethyl-phenyl)-quinolin-4-yl]-propan-1-one (E)-oxime;

1-[2-Methyl-8-(2,4,6-trimethyl-phenyl)-quinolin-4-yl]-propan-1-one (Z)-oxime;

1-[2-Methyl-8-(2,4,6-trimethyl-phenyl)-quinolin-4-yl]-propan-1-one (E)-O-methyl-oxime;

1-[2-Methyl-8-(2,4,6-trimethyl-phenyl)-quinolin-4-yl]-propan-1-one O-methyl-oxime;

1-[2-Methyl-8-(2,4,6-trimethyl-phenyl)-quinolin-4-yl]-propan-1-one O-isobutyl-oxime;

[2-Methyl-8-(2,4,6-trimethyl-phenyl)-quinolin-4-yl]-pyridin-2-yl-methanone O-ethyl-oxime;

Methyl-carbamic acid 2,2,2-trifluoro-1-[2-methyl-8-(2,4,6-trimethyl-phenyl)-quinolin-4-yl]-ethyl ester;
1-Methyl-3-{1-[2-methyl-8-(2,4,6-trimethyl-phenyl)-quinolin-4-yl]-propyl}-urea;
1-[2-Methyl-8-(2,6-dimethyl-4-chloro-phenyl)-quinolin-4-yl]-propan-1-one (E)-oxime;
1-[2-Methyl-8-(2,6-dimethyl-4-chloro-phenyl)-quinolin-4-yl]-propan-1-one (Z)-oxime;
1-[2-Methyl-8-(2-methyl-4-chloro-phenyl)-quinolin-4-yl]-propan-1-one (E)-oxime;
1-[2-Methyl-8-(2-methyl-4-chloro-phenyl)-quinolin-4-yl]-propan-1-one (Z)-oxime;
1-[2-Methyl-8-(2,6-dimethyl-4-bromo-phenyl)-quinolin-4-yl]-propan-1-one (E)-oxime;
1-[2-Methyl-8-(2,6-dimethyl-4-bromo-phenyl)-quinolin-4-yl]-propan-1-one (Z)-oxime;
1-[2-Methyl-8-(2,6-dimethyl-4-methoxy-phenyl)-quinolin-4-yl]-propan-1-one (E)-oxime;
1-[2-Methyl-8-(2,6-dimethyl-4-methoxy-phenyl)-quinolin-4-yl]-propan-1-one (Z)-oxime;
1-[2-Methyl-8-(2,6-dimethyl-4-trifluoromethoxy-phenyl)-quinolin-4-yl]-propan-1-one (E)-oxime;
1-[2-Methyl-8-(2,6-dimethyl-4-trifluoromethoxy-phenyl)-quinolin-4-yl]-propan-1-one (Z)-oxime;
1-[2-Methyl-8-(2,4-dimethyl-phenyl)-quinolin-4-yl]-propan-1-one (E)-oxime;
1-[2-Methyl-8-(2,4-dimethyl-phenyl)-quinolin-4-yl]-propan-1-one (Z)-oxime;
1-[2-Methyl-8-(2,4-dimethoxy-phenyl)-quinolin-4-yl]-propan-1-one (E)-oxime;
1-[2-Methyl-8-(2,4-dimethoxy-phenyl)-quinolin-4-yl]-propan-1-one (Z)-oxime;
1-[2-Methyl-8-(2,4,6-trimethoxy-phenyl)-quinolin-4-yl]-propan-1-one (E)-oxime;
1-[2-Methyl-8-(2,4,6-trimethoxy-phenyl)-quinolin-4-yl]-propan-1-one (Z)-oxime;
1-[2-Methyl-8-(2,6-dimethyl-4-chloro-phenyl)-quinolin-4-yl]-propan-1-one O-methyl-oxime;
1-[2-Methyl-8-(2,6-dimethyl-4-bromo-phenyl)-quinolin-4-yl]-propan-1-one O-methyl-oxime;
1-[2-Methyl-8-(2,6-dimethyl-4-methoxy-phenyl)-quinolin-4-yl]-propan-1-one O-methyl-oxime;
1-[2-Methyl-8-(2,4,6-trimethoxy-phenyl)-quinolin-4-yl]-propan-1-one O-methyl-oxime;
1-[2-Methyl-8-(2,4-dimethoxy-phenyl)-quinolin-4-yl]-propan-1-one O-methyl-oxime;
1-[2-Methyl-8-(2-trifluoromethoxy-4-methoxy-phenyl)-quinolin-4-yl]-propan-1-one O-methyl-oxime;
1-[2-Methyl-8-(2,6-dimethyl-4-chloro-phenyl)-quinolin-4-yl]-propan-1-one O-isobutyl-oxime;
1-[2-Methyl-8-(2,6-dimethyl-4methoxy-phenyl)-quinolin-4-yl]-propan-1-one O-isobutyl-oxime;
1-[2-Methyl-1-(2,6-dimethyl-4-chloro-phenyl)-quinolin-4-yl]-propan-1-one (E)-oxime;
1-[2-Methyl-8-(2,6-dimethyl-4-chloro-phenyl)-quinolin-4-yl]-propan-1-one (Z)-oxime;
1-[2-Methyl-8-(2,6-dimethyl-4-chloro-phenyl)-quinolin-4-yl]-propan-1-one (E)-O-methyl-oxime;
1-[2-Methyl-8-(2,6-dimethyl-4-methoxy-phenyl)-quinolin-4-yl]-propan-1-one (E)-oxime;
1-[2-Methyl-8-(2,6-dimethyl-4-methoxy-phenyl)-quinolin-4-yl]-propan-1-one (Z)-oxime;
1-[2-Methyl-8-(2,6-dimethyl-4-methoxy-phenyl)-quinolin-4-yl]-propan-1-one (E)-O-methyl-oxime;
1-[2-Methyl-8-(2,6-dimethyl-4-chloro-phenyl)-quinolin-4-yl]-propan-1-one O-methyl-oxime;
1-[2-Methyl-8-(2,6-dimethyl-4-methoxyl-phenyl)-quinolin-4-yl]-propan-1-one O-methyl-oxime;
1-[2-Methyl-8-(2,6-dimethyl-4-chloro-phenyl)-quinolin-4-yl]-propan-1-one O-isobutyl-oxime;
[2-Methyl-8(2,6-dimethyl-4-chloro-phenyl)-quinolin-4-yl]-pyridin-2-yl-methanone O-ethyl-oxime;
1-[2-Methyl-8-(2,6-dimethyl-4-methoxy-phenyl)-quinolin-4-yl]-propan-1-one O-isobutyl-oxime;
[2-Methyl-8-(2,6-dimethyl-4-methoxy-phenyl)-quinolin-4-yl]-pyridin-2-yl-methanone O-ethyl-oxime;
Methyl-carbamic acid 2,3,3-trifluoro-1-[2-methyl-8-(2,6-dimethyl-4-chloro-phenyl)-quinolin-4-yl]-ethyl ester;
1-Methyl-3-{1-[2-methyl-8-(2,6-dimethyl-4-chloro-phenyl)-quinolin-4-yl]propyl}-urea;
Methyl-carbamic acid 2,2,2-trifluoro-1-[2-methyl-8-(2,6-dimethyl-4-methoxy-phenyl)-quinolin-4-yl]-ethyl ester; and
1-Methyl-3-{1-[2-methyl8-(2,6-dimethyl-4-methoxy-phenyl)-quinolin-4-yl]-propyl}-urea.

9. A compound of claim 8 selected from the group consisting of:

1-[2-Methyl-8-(2,4,6-trimethyl-phenyl)-quinolin-4-yl]-propan-1-one (E)-oxime;
1-[2-Methyl-8-(2,4,6-trimethyl-phenyl)-quinolin-4-yl]-propan-1-one (Z)-oxime;
(E)1-[2-Methyl-8-(2,4,6-trimethyl-phenyl)-quinolin-4-yl]-propan-1-one O-methyl-oxime;
(Z)-1-[2-Methyl-8-(2,4,6-trimethyl-phenyl)-quinolin-4-yl]-propan-1-one O-methyl-oxime;
1-[2-Methyl-8-(2,4,6-trimethyl-phenyl)-quinolin-4-yl]-propan-1-one O-isobutyl-oxime;
Methyl-carbamic acid 2,2,2-trifluoro-1-[2-methyl-8-(2,4,6-trimethyl-phenyl)-quinolin-4-yl]-ethyl ester; and
1-Methyl-3-{1-[2-methyl-8-(2,4,6-trimethyl-phenyl)-quinolin-4-yl]-propyl}-urea.

10. A pharmaceutical composition for the treatment of (a) a disorder the treatment of which can be effected or facilitated by antagonizing CRF, and disorders induced or facilitated by CRF, or (b) a disorder selected from pain, asthma, psoriasis and allergies; generalized anxiety disorder; panic; phobias; obsessive-compulsive disorder; post-traumatic stress disorder; sleep disorders induced by stress; pain perception and fibromyalgia; mood disorders, depression, and major depression, single episode depression, recurrent depression, child abuse induced depression, mood disorders associated with premenstrual syndrome, and postpartum depression; dysthemia; bipolar disorders; schizophrenia; cyclothymia; chronic fatigue syndrome; stress-induced headache; irritable bowel syndrome, Crohn's disease; spastic colon; post operative ileus; ulcer; diarrhea; stress-induced fever; Parkinson's disease and Huntington's disease; eating disorders, anorexia and bulimia nervosa; hemorrhagic stress; chemical dependencies and addictions drug and alcohol withdrawal symptoms; stress-induced psychotic episodes; euthyroid sick syndrome; syndrome of inappropriate antidiuretic hormone (ADH); obesity; infertility; head traumas; spinal cord trauma; ischemic neuronal damage; excitotoxic neuronal damage; epilepsy; stroke; immune dysfunctions and stress induced immune dysfunctions; muscular spasms; urinary incontinence; multiinfarct dementia; amyotrophic lateral sclerosis; hypertension; tachycardia; congestive heart failure; osteoporosis; premature birth; hypoglycemia; disorders that can be treated by altering circadian rhythm selected from time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents; migraine or non-migraine headache; emesis; and syndrome x, in a mammal, comprising an amount of a compound according to claim 1 that is effective in the treatment of such disorder, and a pharmaceutically acceptable carrier.

11. A method for the treatment of (a) a disorder the treatment of which can be effected or facilitated by antagonizing CRF, and disorders induced or facilitated by CRF, or (b) a disorder selected from pain, asthma, psoriasis and allergies; generalized anxiety disorder; panic; phobias; obsessive-compulsive disorder; post-traumatic stress disorder; sleep disorders induced by stress; pain perception and fibromyalgia; mood disorders, depression, and major depression, single episode depression, recurrent depression, child abuse induced depression, mood disorders associated with premenstrual syndrome, and postpartum depression; dysthemia; bipolar disorders; schizophrenia; cyclothymia; chronic fatigue syndrome; stress-induced headache; irritable bowel syndrome, Crohn's disease; spastic colon; post operative ileus; ulcer; diarrhea; stress-induced fever; Parkinson's disease and Huntington's disease; eating disorders, anorexia and bulimia nervosa; hemorrhagic stress; chemical dependencies and addictions drug and alcohol withdraw symptoms stress-induced psychotic episodes; euthyroid sick syndrome; syndrome of inappropriate antidiuretic hormone (ADH); obesity; infertility; head traumas; spinal cord trauma; ischemic neuronal damage; excitotoxic neuronal damage; epilepsy; stroke, immune dysfunctions and stress induced immune dysfunctions; muscular spasms; urinary incontinence; multiinfarct dementia; amyotrophic lateral sclerosis; hypertension; tachycardia; congestive heart failure; osteoporosis; premature birth; hypoglycemia; disorders that can be treated by altering circadian rhythm selected from time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents; migraine or non-migraine headache; emesis; and syndrome x, in a mammal, comprising administering to a subject in need of said treatment an amount of a compound according to claim 1 that is effective in treating such disorder.

* * * * *